US009441171B2

(12) United States Patent
Ng et al.

(10) Patent No.: US 9,441,171 B2
(45) Date of Patent: *Sep. 13, 2016

(54) FUNCTIONALIZED POLYMERS CONTAINING POLYAMINE SUCCINIMIDE FOR ANTIFOULING IN HYDROCARBON REFINING PROCESSES

(71) Applicant: ExxonMobil Research and Engineering Company, Annandale, NJ (US)

(72) Inventors: ManKit Ng, Annandale, NJ (US); Mohsen Shahmirzadi Yeganeh, Hillsborough, NJ (US); Timothy Andrew Barckholtz, Whitehouse Station, NJ (US); Glen Barry Brons, Phillipsburg, NJ (US); Hong Cheng, Bridgewater, NJ (US); Geoffrey Marshall Keiser, Morris Plains, NJ (US); Donna J. Crowther, Seabrook, TX (US); Patrick Brant, Seabrook, TX (US); David T. Ferrughelli, Flemington, NJ (US); Clarence Chase, Bensalem, PA (US); Emmanuel Ulysse, Maplewood, NJ (US); Edward A. Lemon, Mickleton, NJ (US)

(73) Assignee: EXXONMOBIL RESEARCH AND ENGINEERING COMPANY, Annandale, NJ (US)

( * ) Notice: Subject to any disclaimer, the term of this patent is extended or adjusted under 35 U.S.C. 154(b) by 262 days.

This patent is subject to a terminal disclaimer.

(21) Appl. No.: 13/804,727

(22) Filed: Mar. 14, 2013

(65) Prior Publication Data

US 2014/0262953 A1 Sep. 18, 2014

(51) Int. Cl.
*C10G 75/04* (2006.01)
*C08F 8/32* (2006.01)

(Continued)

(52) U.S. Cl.
CPC .......... *C10G 33/04* (2013.01); *C07D 207/408* (2013.01); *C08F 8/32* (2013.01); *C10G 75/04* (2013.01); *C10L 1/2364* (2013.01); *C10L 1/2383* (2013.01); *C10L 10/04* (2013.01)

(58) Field of Classification Search
CPC .......... C08F 8/32; C08F 8/36; C08F 10/00; C08F 290/04; C08F 222/06; C10G 33/04; C10G 75/04; C10L 1/236; C10L 1/2383; C10L 10/04; C07D 207/408
See application file for complete search history.

(56) References Cited

U.S. PATENT DOCUMENTS 4,368,133 A 1/1983 Forsberg
4,489,194 A 12/1984 Hayashi
(Continued)

FOREIGN PATENT DOCUMENTS

EP 355895 * 2/1990 ............... C08F 8/46
EP 0767182 A2 4/1997
WO 2011014215 A1 2/2011

OTHER PUBLICATIONS

Kropp et al., "Surface-Mediated Reations. 1. Hydrohalogenation of Alkenes and Alkynes", Journal of the American Chemical Society, vol. 112, pp. 7433-7434 (1990).

(Continued)

*Primary Examiner* — Brian McCaig
(74) *Attorney, Agent, or Firm* — Glenn T. Barrett; Andrew T. Ward

(57) ABSTRACT

A multipurpose chemical additives (MPC) is disclosed to mitigate fouling in hydrocarbon refinery processes, such as in a heat exchanger. A method for reducing fouling of a hydrocarbon is also disclosed that includes (i) providing a crude hydrocarbon for a refining process; and (ii) adding an additive to the crude hydrocarbon.

8 Claims, 9 Drawing Sheets

(51) Int. Cl.
*C10G 33/04* (2006.01)
*C10L 1/236* (2006.01)
*C10L 1/2383* (2006.01)
*C10L 10/04* (2006.01)
*C07D 207/408* (2006.01)
*C08F 8/46* (2006.01)
*C08F 10/00* (2006.01)
*C08F 290/04* (2006.01)
*C08F 222/06* (2006.01)

(56) References Cited

U.S. PATENT DOCUMENTS

| | | | |
|---|---|---|---|
| 5,616,153 A * | 4/1997 | Mike et al. | 44/331 |
| 5,777,041 A | 7/1998 | Emert et al. | |
| 6,017,859 A | 1/2000 | Rossi et al. | |
| 6,331,656 B1 | 12/2001 | Blankertz et al. | |
| 8,063,232 B2 | 11/2011 | Hagadorn et al. | |
| 8,283,419 B2 | 10/2012 | Hagadorn et al. | |
| 8,372,930 B2 | 2/2013 | Brant et al. | |
| 8,399,725 B2 | 3/2013 | Brant et al. | |
| 2005/0261440 A1 | 11/2005 | Dickakian et al. | |
| 2009/0318644 A1 | 12/2009 | Brant et al. | |
| 2009/0318646 A1 | 12/2009 | Brant et al. | |
| 2010/0038290 A1 | 2/2010 | Wang et al. | |
| 2010/0170829 A1 | 7/2010 | Ng et al. | |
| 2011/0147275 A1 | 6/2011 | Ng et al. | |
| 2012/0245310 A1 | 9/2012 | Crowther et al. | |
| 2012/0245311 A1 | 9/2012 | Crowther et al. | |
| 2012/0245312 A1 | 9/2012 | Holtcamp et al. | |
| 2012/0245313 A1 | 9/2012 | Crowther et al. | |
| 2012/0309998 A1 | 12/2012 | Holtcamp et al. | |

OTHER PUBLICATIONS

Resconi et al., "Olefin Polymerization at Bis(Pentamethylcyclopentadienyl)Zircornium and -Hafnium Centers: Chain-Transfer Mechanisms", Journal of the American Chemical Society, vol. 114, pp. 1025-1032, (1992).

PCT Application No. PCT/US2014/015990 Communicaton from the International Searching Auhority, Form PCT/ISA/220, dated Oct. 9, 2014, 20 pages.

* cited by examiner

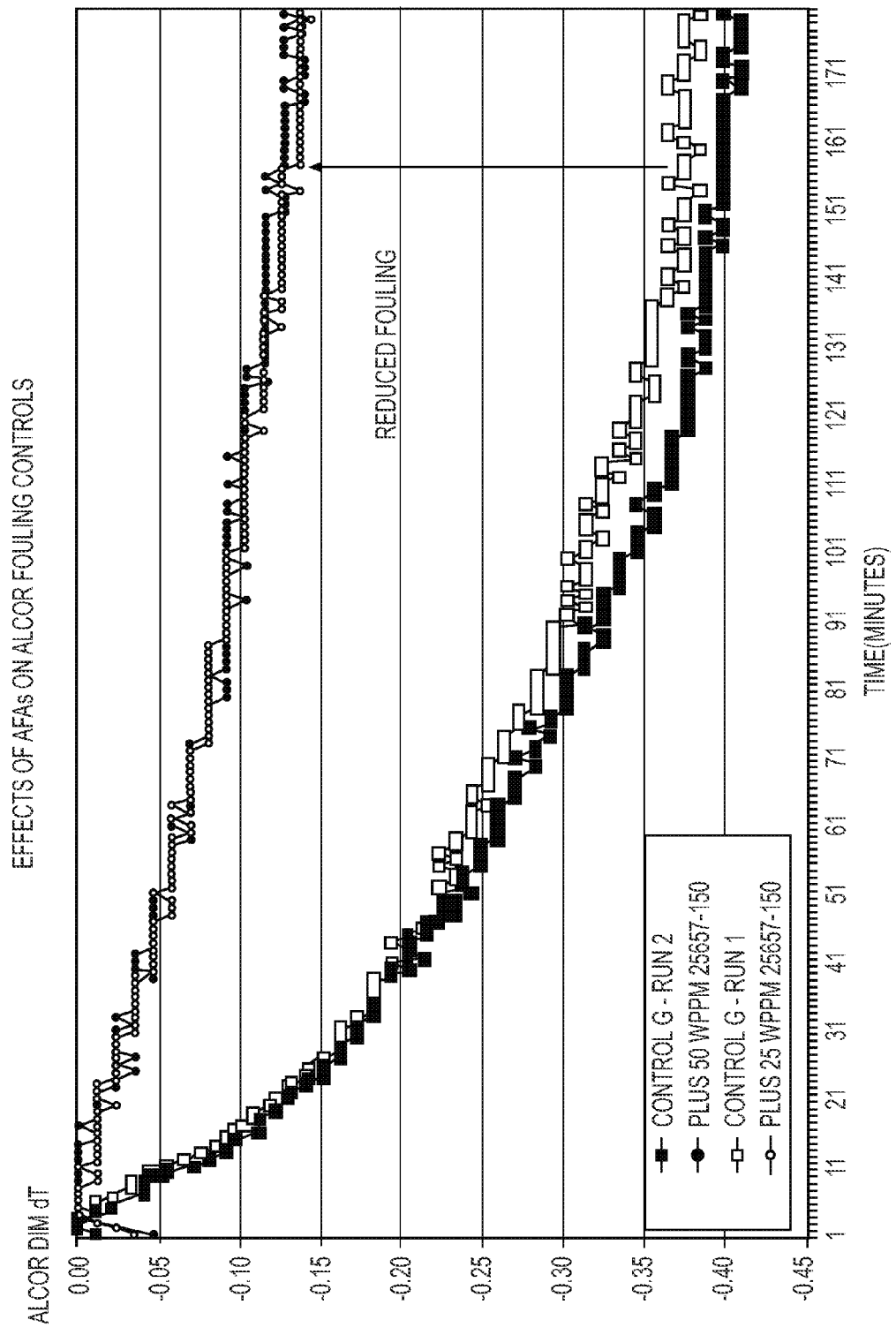

FUNCTIONALIZED POLYMERS CONTAINING POLYAMINE SUCCINIMIDE FOR ANTIFOULING IN HYDROCARBON REFINING PROCESSES

TECHNICAL FIELD

The disclosed subject matter relates to additives to reduce fouling of crude hydrocarbon refinery components, and methods and systems using the same.

BACKGROUND

Crude Pre-Heat Train exchangers are used to heat the crude oil as part of the distillation process. The crude is run on one side of tube-and-shell exchangers and heated by the hot streams run on the opposite side. More typically, crude oil is run through the tube side of the exchangers, however, some refineries run crude through the shell side with the hot stream on the tube side. The crude oil is run through a series of exchangers leading to the desalter and then to the atmospheric furnace. Whole crude oil fouling within exchangers is costly to the petroleum industry due to reduced throughput, energy losses due to needed increased furnace firing and higher cleaning and maintenance costs. In some cases, unplanned unit shut-downs occur due to fouling which adds to the high costs of fouling. To mitigate fouling addition of additives known as anti-foulant additives to crude oil before heat exchanger is a common practice.

Multi-purpose additives can reduce cost in the refining operation. Petroleum refineries incur additional energy costs, perhaps billions per year, due to fouling and the resulting attendant inefficiencies caused by the fouling. More particularly, thermal processing of crude oils, blends and fractions in heat transfer equipment, such as heat exchangers, is hampered by the deposition of insoluble asphaltenes and other contaminants (i.e., particulates, salts, etc.) that may be found in crude oils. Further, the asphaltenes and other organics are known to thermally degrade to coke when exposed to high heater tube surface temperatures.

Fouling in heat exchangers receiving petroleum-type process streams can result from a number of mechanisms including chemical reactions, corrosion, deposit of existing insoluble impurities in the stream, and deposit of materials rendered insoluble by the temperature difference ($\Delta T$) between the process stream and the heat exchanger wall. For example, naturally-occurring asphaltenes can precipitate from the crude oil process stream, thermally degrade to form a coke and adhere to the hot surfaces. Further, the high $\Delta T$ found in heat transfer operations result in high surface or skin temperatures when the process stream is introduced to the heater tube surfaces, which contributes to the precipitation of insoluble particulates. Another common cause of fouling is attributable to the presence of salts, particulates and impurities (e.g., inorganic contaminants) found in the crude oil stream. For example, iron oxide/sulfide, calcium carbonate, silica, sodium chloride and calcium chloride have all been found to attach directly to the surface of a fouled heater rod and throughout the coke deposit. These solids promote and/or enable additional fouling of crude oils.

The buildup of insoluble deposits in heat transfer equipment creates an unwanted insulating effect and reduces the heat transfer efficiency. Fouling also reduces the cross-sectional area of process equipment, which decreases flow rates and desired pressure differentials to provide less than optimal operation. To overcome these disadvantages, heat transfer equipment is ordinarily taken offline and cleaned mechanically or chemically cleaned, resulting in lost production time.

There is a need to reduce precipitation/adherence of particulates and asphaltenes from the heated surface to prevent fouling, particularly before the asphaltenes are thermally degraded or coked. Such reduction will improve the performance of the heat transfer equipment, decrease or eliminate scheduled outages for fouling mitigation efforts, and reduce energy costs associated with the processing activity.

Antifoulant additives have been described in a number of commonly-owned applications, including U.S. Patent Application Publication Nos. 20110147275 and 20100170829, the disclosure of each of which is incorporated herein by reference in its entirety. However, there remains a need for alternative antifoulant additives capable of reducing precipitation and/or adherence of particulates and asphaltenes.

SUMMARY

The disclosed subject matter provide multipurpose chemical additives (MPC) to mitigate fouling in hydrocarbon refinery processes, such as in a heat exchanger. In accordance with one aspect of the disclosed subject matter, a method for reducing fouling a hydrocarbon is provided. The method includes (i) providing a crude hydrocarbon for a refining process; and (ii) adding an additive to the crude hydrocarbon, the additive being represented by one of Formula A and Formula B below:

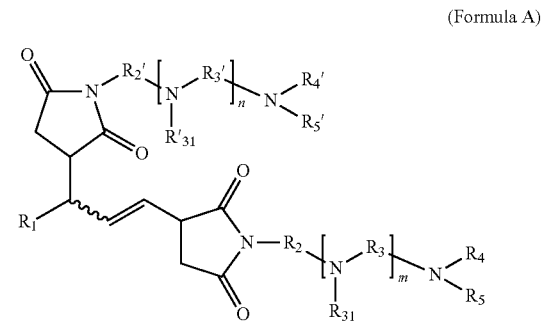

(Formula A)

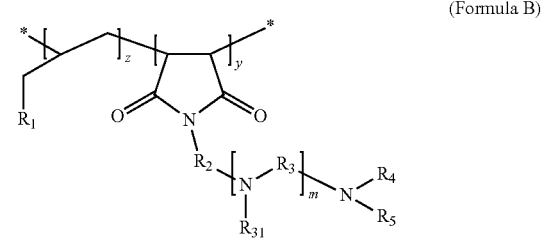

(Formula B)

wherein in each of Formula A and Formula B above:

m is an integer between 0 and 10 inclusive;

$R_1$ is a branched or straight-chained $C_{10}$-$C_{800}$ alkyl or alkenyl group;

$R_2$ is a $C_1$-$C_4$ branched or straight chained alkylene group;

$R_3$ is a $C_1$-$C_4$ branched or straight chained alkylene group;

$R_{31}$ is hydrogen or —$R_8$—$R_9$, wherein $R_8$ is $C_1$-$C_4$ branched or straight chained alkylene group, and $R_9$ is

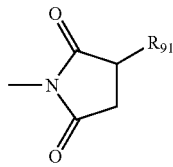

wherein $R_{91}$ is a branched or straight-chained $C_{10}$-$C_{800}$ alkyl or alkenyl group; or $R_8$ and $R_9$ together are a $C_1$-$C_4$ branched or straight chained alkyl group optionally substituted with one or more amine groups; and further wherein the —N($R_{31}$)—$R_3$— repeat unit is optionally interrupted in one or more places by a nitrogen-containing heterocyclic cycloalkyl group; and $R_4$ and $R_5$ are each independently selected from (a) hydrogen; (b) a bond connected to $R_{31}$ in the last distal —N($R_{31}$)—$R_3$— repeat unit; or (c) —$R_6$—$R_7$, wherein $R_6$ is $C_1$-$C_4$ branched or straight chained alkylene group, and $R_7$ is

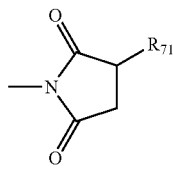

wherein $R_{71}$ is a branched or straight-chained $C_{10}$-$C_{800}$ alkyl or alkenyl group;

wherein in Formula B, n is an integer between 0 and 10 inclusive, and the groups $R_2'$, $R_3'$, $R_{31}'$, $R_4'$ and $R_5'$ are each defined the same as $R_2$, $R_3$, $R_{31}$ and $R_4$, and $R_5$, respectively;

wherein in Formula B, z is 1 or 2, and y is an integer between 1 and 5 inclusive.

According to another aspect of the disclosed subject matter, a compound of Formula A as noted above is provided.

According to another aspect of the disclosed subject matter, a method for preparing a compound for reducing fouling of a crude hydrocarbon in a hydrocarbon refining process is provided. The method includes:

(a) reacting a polymer base unit $R_{11}$, which is a branched or straight-chained $C_{10}$-$C_{800}$ alkyl or alkenyl group having a vinyl terminal group, with maleic anhydride to obtain a polymer represented by Formula I below:

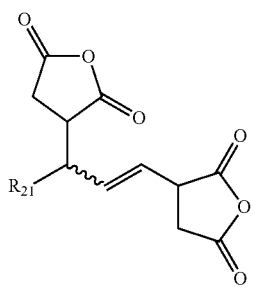

(I)

wherein $R_{21}$ is a branched or straight-chained $C_{10}$-$C_{800}$ alkyl or alkenyl group;

(b) reacting the polymer obtained in (a) with a polyamine represented by

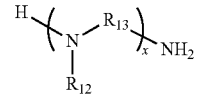

wherein $R_{12}$ is hydrogen or a $C_1$-$C_4$ branched or straight chained alkyl optionally substituted with one or more amine groups, $R_{13}$ is a $C_1$-$C_4$ branched or straight chained alkylene group, and x is an integer between 1 and 10, and further wherein the —N($R_{12}$)—$R_{13}$— unit is optionally interrupted in one or more places by a nitrogen-containing heterocyclic cycloalkyl group, and wherein when the x-th —N($R_{12}$)—$R_{13}$— unit along with the terminal nitrogen atom forms a heterocyclic cycloalkyl group, the terminal —$NH_2$ is replaced by a —NH— group for valency.

According to a further aspect of the disclosed subject matter, a compound prepared by the above method is provided.

According to another aspect of the disclosed subject matter, a method for reducing fouling in a hydrocarbon refinery process is provided. The method includes: providing a crude hydrocarbon for a refining process; and adding an additive to the crude hydrocarbon, the additive represented by Formula A.

According to another aspect of the disclosed subject matter, a compound of Formula B as noted above is provided.

In a further aspect, a method for preparing a compound of Formula B for reducing fouling of a crude hydrocarbon in a hydrocarbon refining process is provided. The method includes:

(a) reacting a polymer base unit $R_{11}$, which is a branched or straight-chained $C_{10}$-$C_{800}$ alkyl or alkenyl group having a vinyl terminal group, with maleic anhydride to obtain a polymer represented by Formula II below:

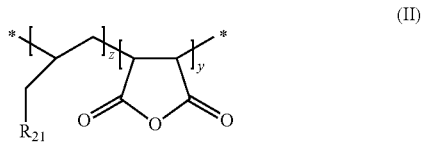

(II)

wherein $R_{21}$ is a branched or straight-chained $C_{10}$-$C_{800}$ alkyl or alkenyl group, z is 1 or 2, and y is an integer between 1 and 5 inclusive;

(b) reacting the polymer obtained in (a) with a polyamine represented by

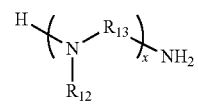

wherein $R_{12}$ is hydrogen or a $C_1$-$C_4$ branched or straight chained alkyl optionally substituted with one or more amine groups, $R_{13}$ is a $C_1$-$C_4$ branched or straight chained alkylene group, and x is an integer between 1 and 10, and further wherein the —N($R_{12}$)—$R_{13}$— unit is optionally interrupted in one or more places by a nitrogen-containing heterocyclic cycloalkyl group, and wherein when the x-th —N($R_{12}$)—$R_{13}$— unit along with the terminal nitrogen atom forms a heterocyclic cycloalkyl group, the terminal —$NH_2$ is replaced by a —NH— group for valency.

In a further aspect, a compound prepared by the above method is provided.

In yet a further aspect, a method for reducing fouling in a hydrocarbon refinery process is provided. The method includes: providing a crude hydrocarbon for a refining process; and adding an additive to the crude hydrocarbon, the additive represented by formula B.

In addition, the disclosed subject matter provides compositions comprising such additives, and systems for refining hydrocarbons containing such additives and compositions.

BRIEF DESCRIPTION OF THE DRAWINGS

The disclosed subject matter will now be described in conjunction with the accompanying drawings in which:

FIG. 9 is a graph demonstrating the effects of fouling of a control crude oil blend sample and a crude oil blend sample treated with 50 wppm and 25 wppm of an additive according to the disclosed subject matter, as measured by the Alcor HLPS apparatus depicted in FIG. 2.

DETAILED DESCRIPTION

Definitions

Figure 1:
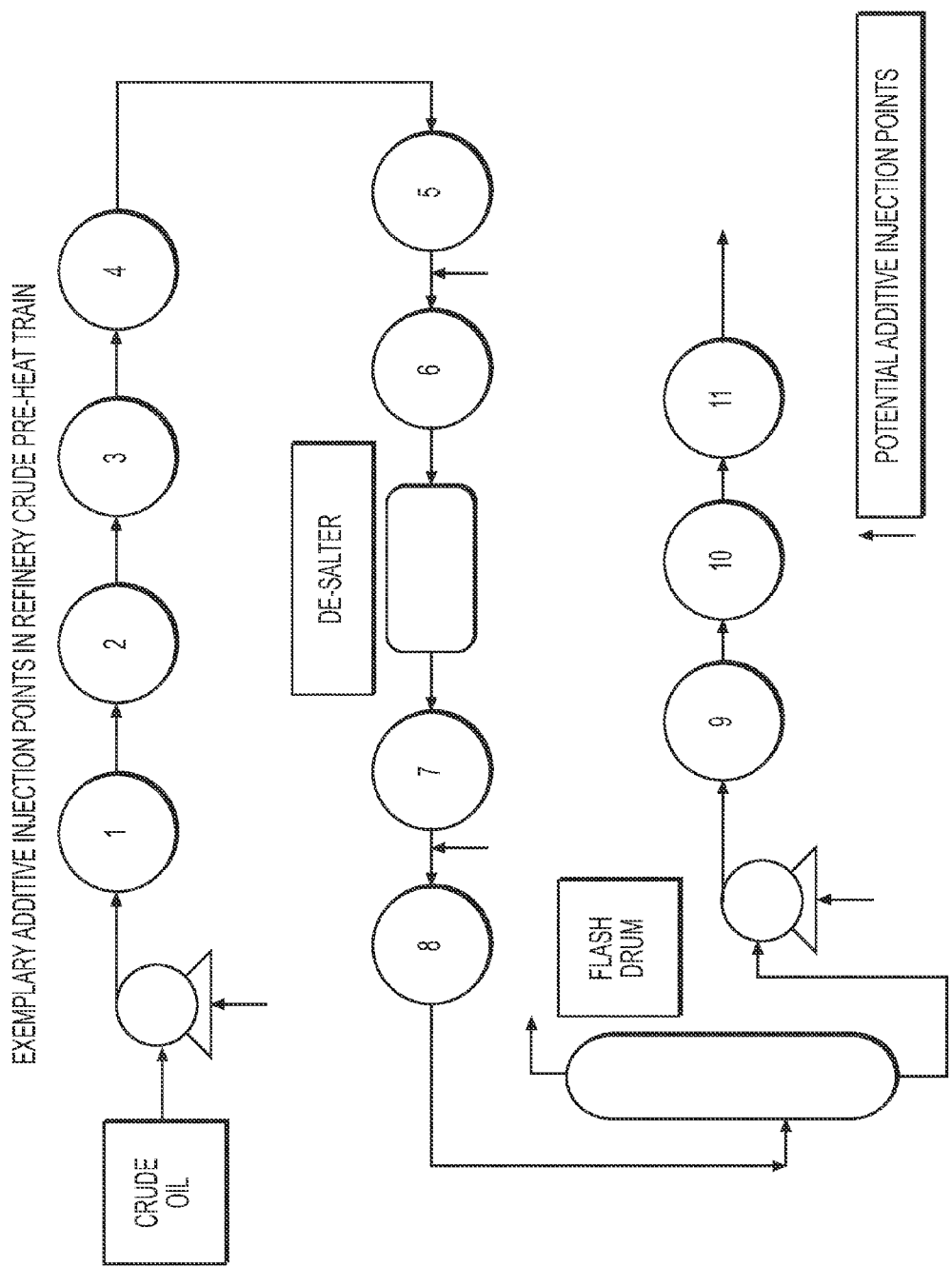
FIG. 1 is a representation of an oil refinery crude pre-heat train, annotated to show non-limiting injection points for the additives of the disclosed subject matter.

The following definitions are provided for purpose of illustration and not limitation.

As used herein, the term "fouling" generally refers to the accumulation of unwanted materials on the surfaces of processing equipment or the like, particularly processing equipment in a hydrocarbon refining process.

As used herein, the term "particulate-induced fouling" generally refers to fouling caused primarily by the presence of variable amounts of organic or inorganic particulates. Organic particulates (such as precipitated asphaltenes and coke particles) include, but are not limited to, insoluble matter precipitated out of solution upon changes in process conditions (e.g., temperature, pressure, or concentration changes) or a change in the composition of the feed stream (e.g., changes due to the occurrence of a chemical reaction). Inorganic particulates include, but are not limited to, silica, iron oxide, iron sulfide, alkaline earth metal oxide, sodium chloride, calcium chloride and other inorganic salts. One major source of these particulates results from incomplete solids removal during desalting and/or other particulate removing processes. Solids promote the fouling of crude oils and blends due to physical effects by modifying the surface area of heat transfer equipment, allowing for longer holdup times at wall temperatures and causing coke formation from asphaltenes and/or crude oil(s).

As used herein, the term "alkyl" refers to a monovalent hydrocarbon group containing no double or triple bonds and arranged in a branched or straight chain.

As used herein, the term "alkylene" refers to a divalent hydrocarbon group containing no double or triple bonds and arranged in a branched or straight chain.

As used herein, the term "alkenyl" refers to a monovalent hydrocarbon group containing one or more double bonds and arranged in a branched or straight chain.

As used herein, a "hydrocarbyl" group refers to any univalent radical that is derived from a hydrocarbon, including univalent alkyl, aryl and cycloalkyl groups.

As used herein, the term "crude hydrocarbon refinery component" generally refers to an apparatus or instrumentality of a process to refine crude hydrocarbons, such as an oil refinery process, which is, or can be, susceptible to fouling. Crude hydrocarbon refinery components include, but are not limited to, heat transfer components such as a heat exchanger, a furnace, a crude preheater, a coker preheater, or any other heaters, a FCC slurry bottom, a debutanizer exchanger/tower, other feed/effluent exchangers and furnace air preheaters in refinery facilities, flare compressor components in refinery facilities and steam cracker/reformer tubes in petrochemical facilities. Crude hydrocarbon refinery components can also include other instrumentalities in which heat transfer can take place, such as a fractionation or distillation column, a scrubber, a reactor, a liquid-jacketed tank, a pipestill, a coker and a visbreaker. It is understood that "crude hydrocarbon refinery components," as used herein, encompasses tubes, piping, baffles and other process transport mechanisms that are internal to, at least partially constitute, and/or are in direct fluid communication with, any one of the above-mentioned crude hydrocarbon refinery components.

As used herein, a reduction (or "reducing") of particulate-induced fouling is generally achieved when the ability of particulates to adhere to heated equipment surfaces is reduced, thereby mitigating their impact on the promotion of the fouling of crude oil(s), blends, and other refinery process streams.

As used herein, reference to a group being a particular polymer (e.g., polypropylene or poly(ethylene-co-propylene) encompasses polymers that contain primarily the respective monomer along with negligible amounts of other substitutions and/or interruptions along polymer chain. In other words, reference to a group being a polypropylene group does not require that the group consist of 100% propylene monomers without any linking groups, substitutions, impurities or other substituents (e.g., alkylene or alkenylene substituents). Such impurities or other substituents can be present in relatively minor amounts so long as they do not affect the industrial performance of the additive, as compared to the same additive containing the respective polymer substituent with 100% purity.

For the purposes of the present application, when a polymer is referred to as comprising an olefin, the olefin present in the polymer is the polymerized form of the olefin.

As used herein, a copolymer is a polymer comprising at least two different monomer units (such as propylene and ethylene). A homo-polymer is a polymer comprising units of the same monomer (such as propylene). A propylene polymer is a polymer having at least 50 mole % of propylene.

The term "vinyl termination", also referred to as "allyl chain end(s)" or "vinyl content" is defined to be a polymer having at least one terminus represented by:

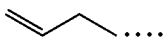

allylic vinyl end group
where the "••••" represents the polymer chain.

In a preferred embodiment the allyl chain end is represented by:

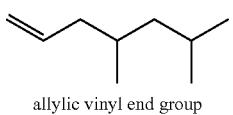

allylic vinyl end group

The amount of allyl chain ends (also called % vinyl termination) is determined using $^1$H NMR at 120° C. using deuterated tetrachloroethane as the solvent on a 500 MHz machine and in selected cases confirmed by $^{13}$C NMR. Resconi has reported proton and carbon assignments (neat perdeuterated tetrachloroethane used for proton spectra while a 50:50 mixture of normal and perdeuterated tetrachloroethane was used for carbon spectra; all spectra were recorded at 100° C. on a Bruker AM 300 spectrometer operating at 300 MHz for proton and 75.43 MHz for carbon) for vinyl terminated propylene polymers in J American Chemical Soc 114 1992, 1025-1032, hereby incorporated by reference in its entirety, that are useful herein.

"Isobutyl chain end" is defined to be a polymer having at least one terminus represented by the formula:

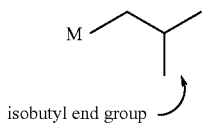

isobutyl end group where M represents the polymer chain. In an example embodiment, the isobutyl chain end is represented by one of the following formulae:

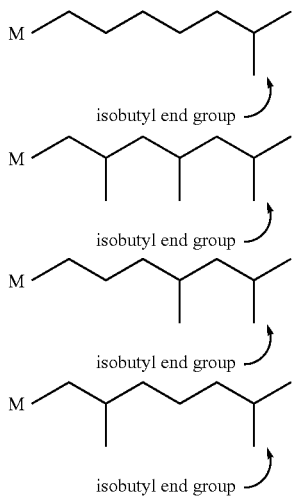

where M represents the polymer chain.

The "isobutyl chain end to allylic vinyl group ratio" is defined to be the ratio of the percentage of isobutyl chain ends to the percentage of allylic vinyl groups.

As used herein, the term "polymer" refers to a chain of monomers having a Mn of 100 g/mol and above.

Reference will now be made to various aspects of the disclosed subject matter in view of the definitions above.

In one aspect, the additives of the disclosed subject matter can interact with the materials in crude oils in a refinery or the like that are prone to cause fouling, e.g., particulate impurities/contaminants and asphaltenes. The interaction can be physical or chemical such as absorption, association, or chemical bonding. The fouling materials can be rendered more soluble in the crude oils as a result of interaction with the antifouling additives, therefore the fouling on the exchanger metal surfaces can be reduced or eliminated.

In accordance with one aspect of the disclosed subject matter, a method for reducing fouling in a hydrocarbon refining process is provided. The method includes (i) providing a crude hydrocarbon for a refining process; and (ii) adding an additive to the crude hydrocarbon, the additive being represented by one of Formula A and Formula B below:

(Formula A)

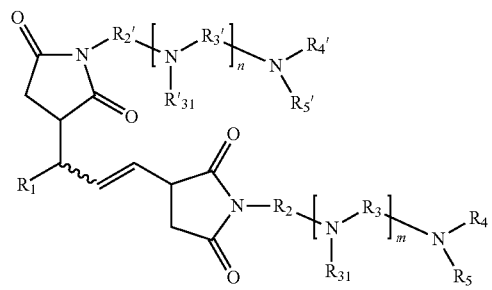

-continued

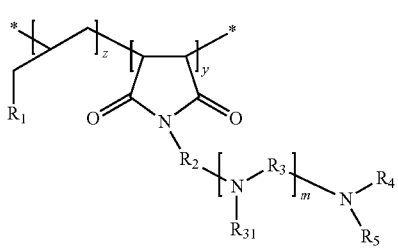

(Formula B)

wherein in each of the Formula A and Formula B above:

m is an integer between 0 and 10 inclusive;

$R_1$ is a branched or straight-chained $C_{10}$-$C_{800}$ alkyl or alkenyl group;

$R_2$ is a $C_1$-$C_4$ branched or straight chained alkylene group;

$R_3$ is a $C_1$-$C_4$ branched or straight chained alkylene group;

$R_{31}$ is hydrogen or —$R_8$—$R_9$, wherein $R_8$ is $C_1$-$C_4$ branched or straight chained alkylene group, and $R_9$ is

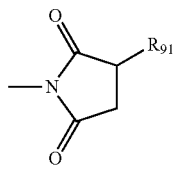

wherein $R_{91}$ is a branched or straight-chained $C_{10}$-$C_{800}$ alkyl or alkenyl group; or $R_8$ and $R_9$ together are a $C_1$-$C_4$ branched or straight chained alkyl group optionally substituted with one or more amine groups; and further wherein the —N($R_{31}$)—$R_3$— repeat unit is optionally interrupted in one or more places by a nitrogen-containing heterocyclic cycloalkyl group; and $R_4$ and $R_5$ are each independently selected from (a) hydrogen; (b) a bond connected to $R_{31}$ in the last distal —N($R_{31}$)—$R_3$— repeat unit; or (c) —$R_6$—$R_7$, wherein $R_6$ is $C_1$-$C_4$ branched or straight chained alkylene group, and $R_7$ is

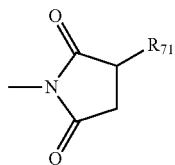

wherein $R_{71}$ is a branched or straight-chained $C_{10}$-$C_{800}$ alkyl or alkenyl group; wherein in Formula A, n is an integer between 0 and 10 inclusive, and the groups $R_2$', $R_3$', $R_{31}$', $R_4$' and $R_5$' are each defined the same as $R_2$, $R_3$, $R_{31}$ and $R_4$, and $R_5$, respectively; and wherein in Formula B, z is 1 or 2, and y is an integer between 1 and 5 inclusive.

In certain embodiments, at least one of $R_1$, $R_{71}$, and $R_{91}$ of the compounds shown above comprises polypropylene (PP), which can be atactic polypropylene or isotactic polypropylene. The polypropylene can be amorphous, and can include isotactic or syndiotactic crystallizable units. In some embodiments, the polypropylene includes meso diads constituting from about 30% to about 99.5% of the total diads of the polypropylene. In alternative embodiments, at least one of $R_1$, $R_{71}$, and $R_{91}$ of the compounds above comprises polyethylene (PE).

In a further embodiment, at least one of $R_1$, $R_{71}$, and $R_{91}$ of the compounds above comprises poly(ethylene-co-propylene) (EP). The mole percentage of the ethylene units and propylene units in the poly(ethylene-co-propylene) can vary. For example, in some embodiments, the poly(ethylene-co-propylene) can contain about 1 to about 90 mole % of ethylene units and about 99 to about 10 mole % propylene units. In other embodiments, the poly(ethylene-co-propylene) can contain about 10 to about 90 mole % of ethylene units and about 90 to about 10 mole % propylene units. In certain embodiments, the poly(ethylene-co-propylene) contains about 10 to about 50 mole % of ethylene units.

In some embodiments of the above method, at least one of $R_1$, $R_{71}$, and $R_{91}$ of the additive of Formula I has a number-averaged molecular weight of from about 300 to about 30,000 g/mol (assuming one olefin unsaturation per chain, as measured by $^1$H NMR). Alternatively, at least one of $R_1$, $R_{71}$, and $R_{91}$ of the compounds above has a number-averaged molecular weight (Mn) of from about 500 to 5,000 g/mol. In one embodiment, the PP or EP included in the $R_1$, $R_{71}$ or $R_{91}$ of the compounds above, individually, has a molecular weight from about 300 to about 30,000 g/mol (and as high as 60K or 60,000 g/mol.), or from about 500 to about 5000 g/mol. In one embodiment, the PP or EP groups have a molecular weight, individually, ranging from about 500 to about 2500 g/mol, or a molecular weight (Mn) of from about 500 to about 650 g/mol, or a molecular weight of from about 800 to about 1000 g/mol, or a molecular weight of from about 2000 to about 2500 g/mol.

In other embodiments of the compound, at least one of $R_1$, $R_{71}$, and $R_{91}$ comprises poly(higher alpha-olefin) or polypropylene-co-higher alpha-olefin), the higher alpha-olefin including two or more carbon atoms on each side chain. For example, suitable higher alpha-olefins can include, but are not limited to, 1-butene, 1-pentene, 1-hexene, 1-heptene, 1-octene, 1-nonene, 1-decene, 1-undecene, 1-dodecene, 1-tridecene, 1-tetradecene, 1-hexadecene, 1-octadecene and the like.

In certain embodiments of the above compound, the nitrogen content in the compound of Formula I is about 1 wt % to about 10 wt % based on the total weight of the compound.

In certain embodiments, $R_3$ is —$CH_2$—$CH_2$—, and $R_{31}$ is hydrogen. In these embodiments, the —N($R_{31}$)—$R_3$— repeat unit can be interrupted in one or more places by a 1,4-diethylenediamine.

With reference to Formula A, and in accordance with another aspect of the subject matter disclosed herein, a method for preparing a compound for reducing fouling in a hydrocarbon refining process is provided. The method includes:

(a) reacting a polymer base unit $R_{11}$, which is a branched or straight-chained $C_{10}$-$C_{800}$ alkyl or alkenyl group having a vinyl terminal group, with maleic anhydride to obtain a polymer represented by Formula I below:

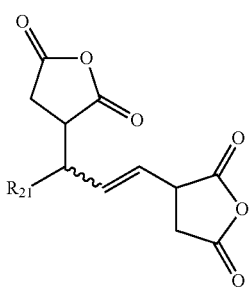

(I)

wherein $R_{21}$ is a branched or straight-chained $C_{10}$-$C_{800}$ alkyl or alkenyl group;

(b) reacting the polymer obtained in (a) with a polyamine represented by

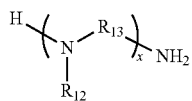

wherein $R_{12}$ is hydrogen or a $C_1$-$C_4$ branched or straight chained alkyl optionally substituted with one or more amine groups, $R_{13}$ is a $C_1$-$C_4$ branched or straight chained alkylene group, and x is an integer between 1 and 10, and further wherein the —N($R_{12}$)—$R_{13}$— unit is optionally interrupted in one or more places by a nitrogen-containing heterocyclic cycloalkyl group, and wherein when the x-th —N($R_{12}$)—$R_{13}$— unit along with the terminal nitrogen atom forms a heterocyclic cycloalkyl group, the terminal —$NH_2$ is replaced by a —NH— group for valency.

In certain embodiments of the above methods, the polymer base unit $R_{11}$ has a number-averaged molecular weight of 300 to 30,000 g/mol (assuming one olefin unsaturation per chain, as measured by $^1H$ NMR), and alternatively, about 500 to 5,000 g/mol.

In some embodiments of the above methods, the polymer base unit $R_{11}$ comprises polypropylene. The polypropylene can be either atactic polypropylene or isotactic polypropylene. The polypropylene can be amorphous, and can include isotactic or syndiotactic crystallizable units. In some embodiments, the polypropylene includes meso diads constituting from about 30% to about 99.5% of the total diads of the polypropylene. The polymer base unit $R_{11}$ can also comprise polyethylene.

In alternative embodiments, the polymer base unit $R_{11}$ comprises poly(ethylene-co-propylene). The poly(ethylene-co-propylene) can contain from about 1 or 10 mole % to about 90 or 99 mole % of ethylene units and from about 99 or 90 mole % to about 10 or 1 mole % propylene units. In one embodiment, the poly(ethylene-co-propylene) polymer contains from about 2 or 20 mole % to about 50 mole % ethylene units.

In one embodiment, the PP or EP included in $R_{11}$ to form Formula I individually has a number-averaged molecular weight (Mn) from about 300 to about 30,000 g/mol, or from about 500 to about 5000 g/mol (assuming one olefin unsaturation per chain, as measured by $^1H$ NMR). In one embodiment, the PP or EP groups have a molecular weight (Mn), individually, ranging from about 500 to about 2500 g/mol, or a molecular weight of from about 500 to about 650 g/mol, or a molecular weight of from about 800 to about 1000 g/mol, or a molecular weight of from about 2000 to about 2500 g/mol.

In embodiments where the polymer base unit $R_{11}$ includes polypropylene or poly(ethylene-co-propylene), such groups can be prepared, for example, by metallocene-catalyzed polymerization of propylene or a mixture of ethylene and propylene, which are then terminated with a high vinyl group content in the chain end. The number-averaged molecular weight ($M_n$) of the PP or EP can be from about 300 to about 30,000 g/mol, as determined by $^1H$ NMR spectroscopy. The vinyl-terminated atactic or isotactic polypropylenes (v-PP) or vinyl-terminated poly(ethylene-co-propylene) (v-EP) suitable for further chemical functionalization can have a molecular weight ($M_n$) approximately from about 300 to about 30,000 g/mol, and preferably about 500 to 5,000 g/mol. The terminal olefin group can be a vinylidene group or an allylic vinyl group (both covered in Formula I). In certain embodiments, the terminal olefin group is an allylic vinyl group. In this regard, the terminal allylic vinyl group rich PP or EP as disclosed in U.S. Pat. No. 8,372,930 and co-pending application U.S. Patent Application Publication No. 20090318646, can be used, which are both hereby incorporated by reference in their entirety. Some of the vinyl terminated EP or PP according to these co-pending applications contains more than 90% of allylic terminal vinyl group.

In some embodiments of the above methods, $R_{11}$ can comprise propylene and less than 0.5 wt % comonomer, preferably 0 wt % comonomer, wherein the $R_{11}$ has:
i) at least 93% allyl chain ends (preferably at least 95%, preferably at least 97%, preferably at least 98%);
ii) a number average molecular weight (Mn) of about 500 to about 20,000 g/mol, as measured by $^1H$ NMR, assuming one olefin unsaturation per chain (preferably 500 to 15,000, preferably 700 to 10,000, preferably 800 to 8,000 g/mol, preferably 900 to 7,000, preferably 1000 to 6,000, preferably 1000 to 5,000);
iii) an isobutyl chain end to allylic vinyl group ratio of 0.8:1 to 1.3:1.0;
iv) less than 1400 ppm aluminum, (preferably less than 1200 ppm, preferably less than 1000 ppm, preferably less than 500 ppm, preferably less than 100 ppm).

In some embodiments of the above methods, $R_{11}$ can comprise a propylene copolymer having an Mn of 300 to 30,000 g/mol as measured by 1H NMR and assuming one olefin unsaturation per chain (preferably 400 to 20,000, preferably 500 to 15,000, preferably 600 to 12,000, preferably 800 to 10,000, preferably 900 to 8,000, preferably 900 to 7,000 g/mol), comprising 10 to 90 mol % propylene (preferably 15 to 85 mol %, preferably 20 to 80 mol %, preferably 30 to 75 mol %, preferably 50 to 90 mol %) and 10 to 90 mol % (preferably 85 to 15 mol %, preferably 20 to 80 mol %, preferably 25 to 70 mol %, preferably 10 to 50 mol %) of one or more alpha-olefin comonomers (preferably ethylene, butene, hexene, or octene, or decene, preferably ethylene), wherein the polymer has at least X % allyl chain ends (relative to total unsaturations), where X is 80% or more, preferably 85% or more, preferably 90% or more, preferably 95% or more. Alternatively, $R_{11}$ can have at least 80% isobutyl chain ends (based upon the sum of isobutyl and n-propyl saturated chain ends), preferably at least 85% isobutyl chain ends, preferably at least 90% isobutyl chain ends. Alternately, $R_{11}$ can have an isobutyl chain end to allylic vinyl group ratio of 0.8:1 to 1.35:1.0, preferably 0.9:1 to 1.20:1.0, preferably 0.9:1.0 to 1.1:1.0.

In other embodiments, $R_{11}$ can comprise a polypropylene copolymer having more than 90 mol % propylene (preferably 95 to 99 mol %, preferably 98 to 9 mol %) and less than 10 mol % ethylene (preferably 1 to 4 mol %, preferably 1 to 2 mol %), wherein the copolymer has:

at least 93% allyl chain ends (preferably at least 95%, preferably at least 97%, preferably at least 98%);

a number average molecular weight (Mn) of about 400 to about 30,000 g/mol, as measured by $^1$H NMR and assuming one olefin unsaturation per chain (preferably 500 to 20,000, preferably 600 to 15,000, preferably 700 to 10,000 g/mol, preferably 800 to 9,000, preferably 900 to 8,000, preferably 1000 to 6,000);

an isobutyl chain end to allylic vinyl group ratio of 0.8:1 to 1.35:1.0, and less than 1400 ppm aluminum, (preferably less than 1200 ppm, preferably less than 1000 ppm, preferably less than 500 ppm, preferably less than 100 ppm).

In alternative embodiments, $R_{11}$ can comprise a polypropylene copolymer comprising:

at least 50 (preferably 60 to 90, preferably 70 to 90) mol % propylene and from 10 to 50 (preferably 10 to 40, preferably 10 to 30) mol % ethylene, wherein the polymer has:

at least 90% allyl chain ends (preferably at least 91%, preferably at least 93%, preferably at least 95%, preferably at least 98%);

an Mn of about 150 to about 20,000 g/mol, as measured by $^1$H NMR and assuming one olefin unsaturation per chain (preferably 200 to 15,000, preferably 250 to 15,000, preferably 300 to 10,000, preferably 400 to 9,500, preferably 500 to 9,000, preferably 750 to 9,000); and an isobutyl chain end to allylic vinyl group ratio of 0.8:1 to 1.3:1.0, wherein monomers having four or more carbon atoms are present at from 0 to 3 mol % (preferably at less than 1 mol %, preferably less than 0.5 mol %, preferably at 0 mol %).

In further embodiments, $R_{11}$ can comprise a polypropylene copolymer comprising:

at least 50 (preferably at least 60, preferably 70 to 99.5, preferably 80 to 99, preferably 90 to 98.5) mol % propylene, from 0.1 to 45 (preferably at least 35, preferably 0.5 to 30, preferably 1 to 20, preferably 1.5 to 10) mol % ethylene, and from 0.1 to 5 (preferably 0.5 to 3, preferably 0.5 to 1) mol % $C_4$ to $C_{12}$ olefin (such as butene, hexene or octene, or decene, preferably butene), wherein the polymer has:

at least 90% allyl chain ends (preferably at least 91%, preferably at least 93%, preferably at least 95%, preferably at least 98%);

a number average molecular weight (Mn) of about 150 to about 15,000 g/mol, as measured by $^1$H NMR and assuming one olefin unsaturation per chain (preferably 200 to 12,000, preferably 250 to 10,000, preferably 300 to 10,000, preferably 400 to 9500, preferably 500 to 9,000, preferably 750 to 9,000); and an isobutyl chain end to allylic vinyl group ratio of 0.8:1 to 1.35:1.0.

In certain embodiments, $R_{11}$ can comprise a polypropylene copolymer comprising:

at least 50 (preferably at least 60, preferably 70 to 99.5, preferably 80 to 99, preferably 90 to 98.5) mol % propylene, from 0.1 to 45 (preferably at least 35, preferably 0.5 to 30, preferably 1 to 20, preferably 1.5 to 10) mol % ethylene, and from 0.1 to 5 (preferably 0.5 to 3, preferably 0.5 to 1) mol % diene (such as $C_4$ to $C_{12}$ alpha-omega dienes (such as butadiene, hexadiene, octadiene), norbornene, ethylidene norbornene, vinylnorbornene, norbornadiene, and dicyclopentadiene), wherein the polymer has:

at least 90% allyl chain ends (preferably at least 91%, preferably at least 93%, preferably at least 95%, preferably at least 98%);

a number average molecular weight (Mn) of about 150 to about 20,000 g/mol, as measured by $^1$H NMR and assuming one olefin unsaturation per chain (preferably 200 to 15,000, preferably 250 to 12,000, preferably 300 to 10,000, preferably 400 to 9,500, preferably 500 to 9,000, preferably 750 to 9,000); and an isobutyl chain end to allylic vinyl group ratio of 0.7:1 to 1.35:1.0.

In other embodiments of the above methods, $R_{11}$ can comprise poly(higher alpha-olefin) or poly(propylene-co-higher alpha-olefin), the higher alpha-olefin including two or more carbon atoms on each side chain. For example, suitable higher alpha-olefins can include, but are not limited to, 1-butene, 1-pentene, 1-hexene, 1-heptene, 1-octene, 1-nonene, 1-decene, 1-undecene, 1-dodecene, 1-tridecene, 1-tetradecene, 1-hexadecene, 1-octadecene and the like.

In certain embodiments, $R_{11}$ includes those vinyl terminated macromonomers disclosed in U.S. Patent Application Publication Nos. 20120245312, 20120245310, 20120245311, 20120245313, and U.S. Provisional Application No. 61/704,604, the disclosure of each of which is incorporated by reference in its entirety herein.

In the above method of preparation, maleic anhydride can be used for the reaction of converting a polymer base unit $R_{11}$ having a terminal vinyl functionality to a compound of Formula I. The reaction can proceed through a thermal condition (e.g., at temperature of about 150° C. to 260° C.) without using external radical providers, such as a peroxide initiator. Under this condition, a compound of Formula I can be obtained, along with a polymer having a mono-succinic anhydride terminal group. For example and as embodied herein, the thermal reaction between $R_{11}$ and maleic anhydride can be illustrated below in Scheme 1 using a vinyl terminated polypropylene as an example of $R_{11}$.

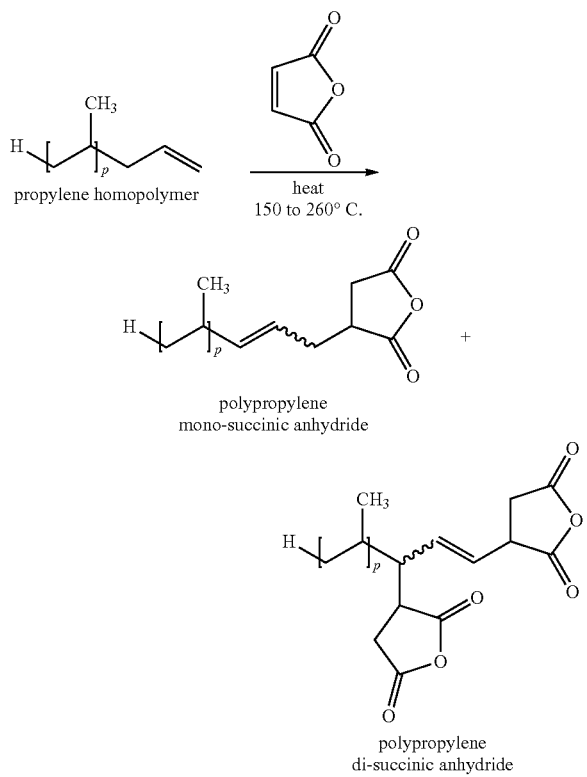

Scheme 1

The above reaction can be carried out without the use of any solvent. Alternatively, any inert solvent (e.g., paraffinic solvent, naphthenic solvent, aromatic solvent, halogenated solvent, mineral oil, synthetic fluid, etc.) with appropriate boiling point or boiling point range can be used. The reaction can be conducted in an open system under atmospheric pressure by using standard laboratory glassware or in a closed system by using an autoclave (or any sealed vessel suitable for holding the pressure). A catalyst can also be used to increase the rate of reaction between the hydrocarbon copolymer and the unsaturated carboxylic acid derivative.

The vinyl terminated polymer can also be a copolymer of polypropylene, for example, poly-ethylene-propylene, or poly-propylene-higher alpha-olefin. In such cases, the reactions under a thermal condition can be illustrated below in Scheme 2 and Scheme 3, respectively.

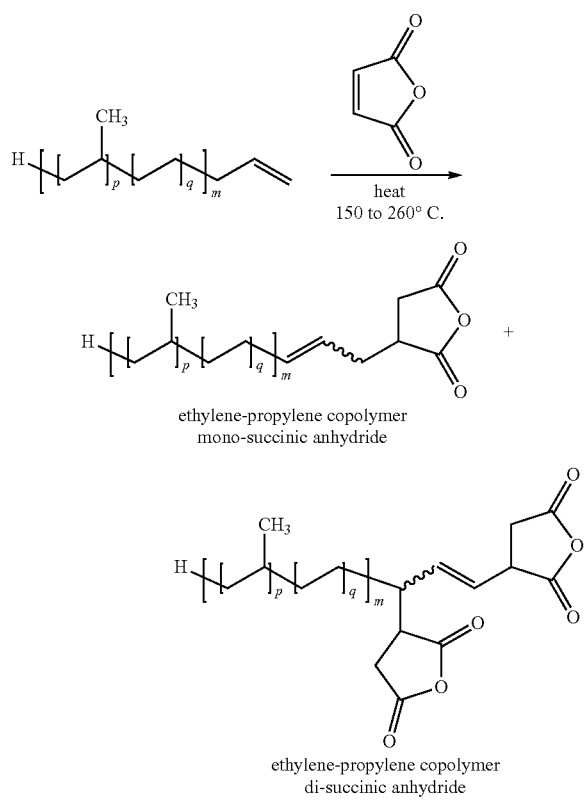

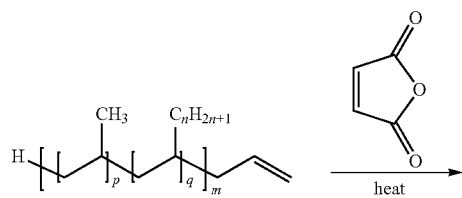

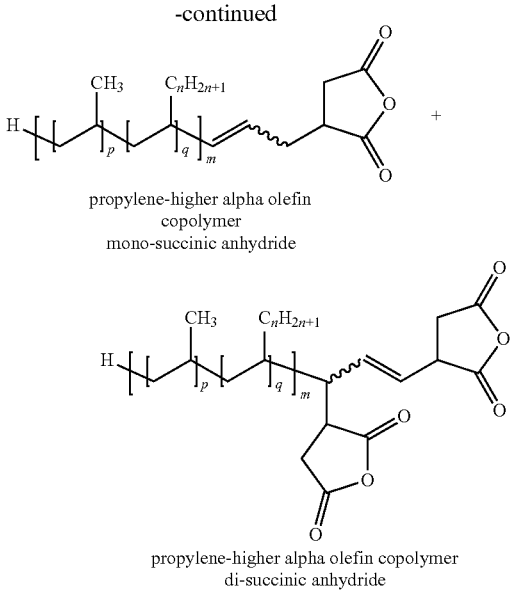

propylene-higher alpha olefin copolymer mono-succinic anhydride propylene-higher alpha olefin copolymer di-succinic anhydride The above reactions can be performed at temperatures between about 150° C. to about 260° C. and between about atmospheric pressure to about 500 psi. The reaction can be conducted in an open system under atmospheric pressure by using standard laboratory glassware or in a closed system by using an autoclave (or any sealed vessel suitable for maintaining pressure). Reaction time can vary from minutes to hours depending on the conditions used. The rate of reaction will increase with increased temperature and pressure. At temperatures between about 220-260° C. at elevated pressure, high conversion of the vinyl-terminated polymers can be achieved within about two hours.

The charge ratio of vinyl-terminated polymers to maleic anhydride in the reactions depicted in Scheme 1, Scheme 2 and Scheme 3 can vary from about 1:1 to about 1:10, or preferably from about 1:1 to about 1:6, or preferably from about 1:1 to about 1:4, or preferably from about 1:1 to about 1:3, or preferably from about 1:1 to about 1:2, or preferably from about 1:1 to about 1:1.5, or preferably from about 1:1 to about 1:1.2. Increasing the charge ratio of maleic anhydride to vinyl-terminated polymer will increase the proportion of di-succinic anhydride product and decrease the proportion of mono-succinic anhydride product. Additionally, at a given temperature, increasing the reaction time will increase the proportion of di-succinic anhydride reaction products relative to mono-succinic anhydride products, provided that sufficient maleic anhydride is present in the reaction system.

The method of preparing the compound of Formula A can include reacting the succinic anhydride-containing polymers obtained above with a polyamine (PAM). The reaction can proceed through a condensation mechanism. The polyamine can include linear, branched or cyclic isomers of an oligomer of ethyleneamine, or mixtures thereof, wherein each two neighboring nitrogens in the oligomer of ethyleneamine are bridged by one or two ethyleneamine groups. For example, the polyamine can be selected from polyethyleneamines with general molecular formula $H_2N(CH_2CH_2NH)_xH$ (where x=1, 2, 3, . . . ) such as ethylenediamine, diethylenetriamine, triethylenetetramine, tetraethylenepentamine, pentaethylenehexamine, hexaethyleneheptamine, and mixtures thereof. In some embodiments, the polyamine can comprise a heavy polyamine, such as polyethyleneamine heavy bottoms available from Dow Chemical as "Heavy Polyamine X" or HPA-X.

Using a reaction between the products of Scheme 3 and tetraethylenepentamine as an example of PAM, the condensation reaction can be illustrated below in Scheme 4.

Scheme 4

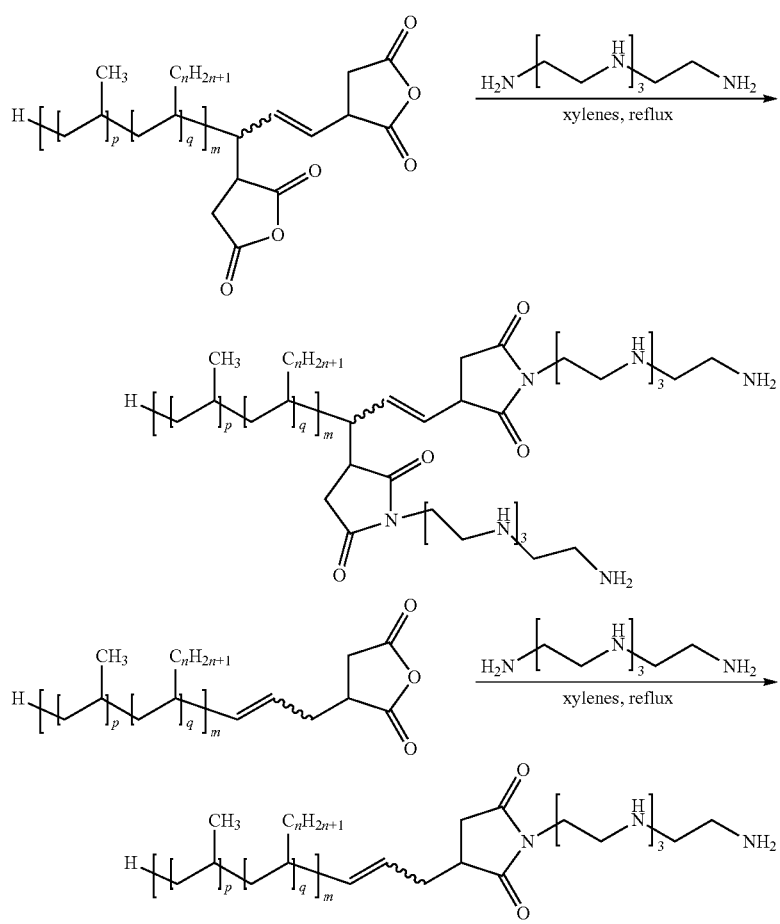

In additional embodiments of the disclosed subject matter, nucleophilic reagents other than polyamines can be used to functionalize the compounds of Formula I. These reagents include, for example, monoamines, diamines, amino alcohols, polyetheramines, polyols, polyalkylene glycols, polyalkylene polyamine and the like.

Furthermore, vinylidene-terminated polymer or copolymer (e.g., ethylene-propylene copolymer, and propylene-higher alpha-olefin copolymer) can also be used as $R_{11}$. Illustrations for using vinylidene-terminated polypropylene and vinylidene-terminated propylene-higher alpha-olefin copolymer as $R_{11}$ are shown below in Scheme 5 and Scheme 6, respectively.

Scheme 5

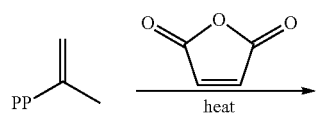

vinylidene-terminated macromer
PP = polypropylene

-continued

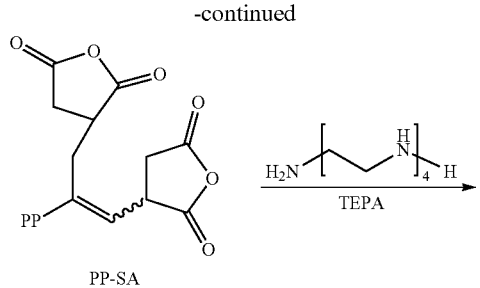

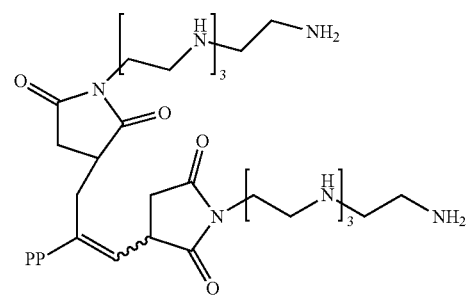

Scheme 6

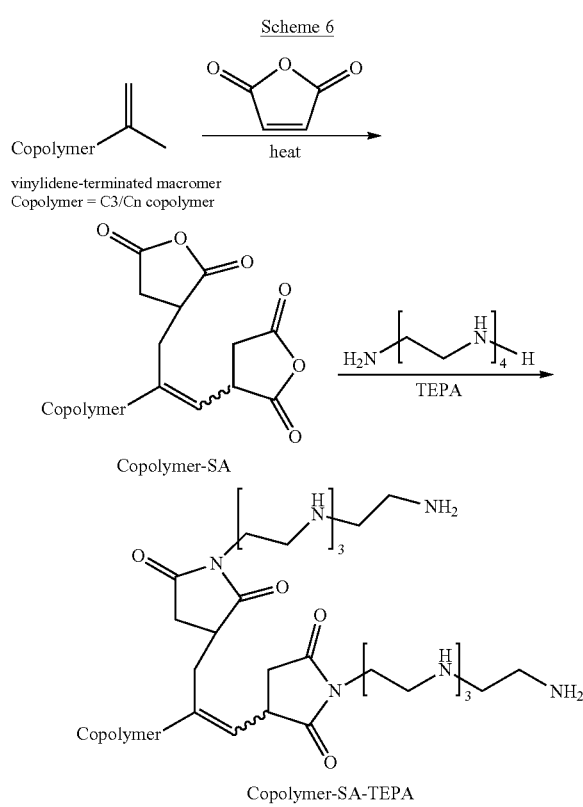

Copolymer-SA-TEPA

As a result of the amination reactions, the number of polymer chain attached to each polyamine molecule can vary from one to two to three or more. In addition, both primary and secondary amino groups on the polyamine can participate in the reaction with the anhydride-functionalized polymer. Other commercially available lower or higher polyamines with linear, branched, cyclic or heterocyclic structures can also be used. It is well-known and understood by those skilled in the art that these polyamines can be mixtures of compounds comprised of molecules with a distribution of chain lengths, different level and type of amine (primary, secondary, and tertiary) functional groups, and varying degree of linear, branched and cyclic structures. For example, possible isomers for tetraethylenepentamine include the following:

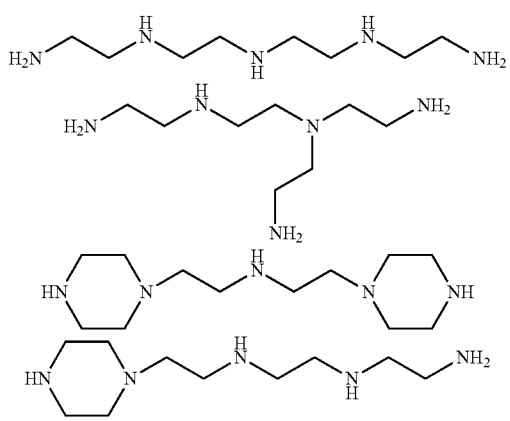

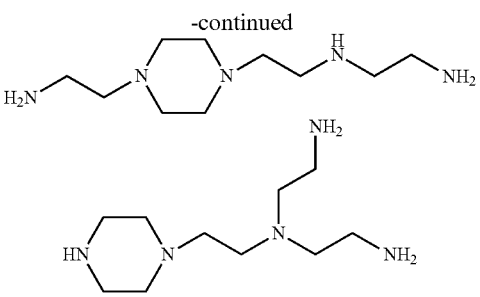

As the molecular weight of polyamines increases, the number of possible isomers increases as well.

In a further aspect, a method for preparing a compound according to Formula B for treating an emulsion of crude hydrocarbon and/or reducing fouling in a hydrocarbon refining process is provided. The method includes:

(a) reacting a polymer base unit $R_{11}$, which is a branched or straight-chained $C_{10}$-$C_{800}$ alkyl or alkenyl group having a vinyl terminal group, with maleic anhydride in the presence of a radical initiator to obtain a polymer represented by Formula II below:

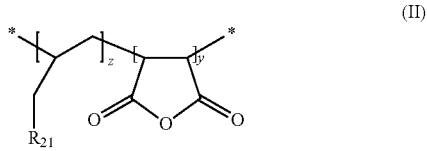

(II)

wherein $R_{21}$ is a branched or straight-chained $C_{10}$-$C_{800}$ alkyl or alkenyl group, z is 1 or 2, and y is an integer between 1 and 5 inclusive;

(b) reacting the polymer obtained in (a) with a polyamine represented by

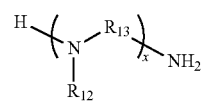

wherein $R_{12}$ is hydrogen or a $C_1$-$C_4$ branched or straight chained alkyl optionally substituted with one or more amine groups, $R_{13}$ is a $C_1$-$C_4$ branched or straight chained alkylene group, and x is an integer between 1 and 10, and further wherein the —$N(R_{12})$—$R_{13}$— unit is optionally interrupted in one or more places by a nitrogen-containing heterocyclic cycloalkyl group, and wherein when the x-th —$N(R_{12})$—$R_{13}$— unit along with the terminal nitrogen atom forms a heterocyclic cycloalkyl group, the terminal —$NH_2$ is replaced by a —NH— group for valency.

In certain embodiments of the above methods, the polymer base unit $R_{11}$ has a number-averaged molecular weight of 300 to 30,000 g/mol (assuming one olefin unsaturation per chain, as measured by $^1$H NMR), and alternatively, about 500 to 5,000 g/mol.

In some embodiments of the above methods, the polymer base unit $R_{11}$ comprises polypropylene. The polypropylene can be either atactic polypropylene or isotactic polypropylene. The polypropylene can be amorphous, and can include isotactic or syndiotactic crystallizable units. In some embodiments, the polypropylene includes meso diads constituting from about 30% to about 99.5% of the total diads of the polypropylene. The polymer base unit $R_{11}$ can also comprise polyethylene.

In alternative embodiments, the polymer base unit $R_{11}$ comprises poly(ethylene-co-propylene). The poly(ethylene-co-propylene) can contain from about 1 or 10 mole % to about 90 or 99 mole % of ethylene units and from about 99 or 90 mole % to about 10 or 1 mole % propylene units. In one embodiment, the poly(ethylene-co-propylene) polymer contains from about 2 or 20 mole % to about 50 mole % ethylene units.

In one embodiment, the PP or EP included in the $R_{11}$ to form Formula II individually has a number-averaged molecular weight ($M_n$) from about 300 to about 30,000 g/mol, or from about 500 to about 5000 g/mol (assuming one olefin unsaturation per chain, as measured by $^1$H NMR). In one embodiment, the PP or EP groups have a molecular weight, individually, ranging from about 500 to about 2500 g/mol, or a molecular of from about 500 to about 650 g/mol, or a molecular weight of from about 800 to about 1000 g/mol, or a molecular weight of from about 2000 to about 2500 g/mol.

In embodiments where the polymer base unit $R_{11}$ include polypropylene or poly(ethylene-co-propylene), such groups can be prepared, for example, by metallocene-catalyzed polymerization of propylene or a mixture of ethylene and propylene, which are then terminated with a high vinyl group content in the chain end. The number-averaged molecular weight ($M_n$) of the PP or EP can be from about 300 to about 30,000 g/mol, as determined by $^1$H NMR spectroscopy. The vinyl-terminated atactic or isotactic polypropylenes (v-PP) or vinyl-terminated poly(ethylene-co-propylene) (v-EP) suitable for further chemical functionalization can have a molecular weight ($M_n$) approximately from about 300 to about 30,000 g/mol, and preferably about 500 to 5,000 g/mol. The terminal olefin group can be a vinylidene group or an allylic vinyl group. In certain embodiments, the terminal olefin group is an allylic vinyl group. In this regard, the terminal allylic vinyl group rich PP or EP as disclosed in U.S. Pat. No. 8,372,930 and co-pending application, U.S. Patent Application Publication No. 20090318646, can be used, each of which is hereby incorporated by reference in its entirety. Some of the vinyl terminated EP or PP according to these co-pending applications contains more than 90% of allylic terminal vinyl group.

In some embodiments of the above methods, $R_{11}$ can comprise propylene and less than 0.5 wt % comonomer, preferably 0 wt % comonomer, wherein the $R_{11}$ has:
  i) at least 93% allyl chain ends (preferably at least 95%, preferably at least 97%, preferably at least 98%);
  ii) a number average molecular weight (Mn) of about 500 to about 20,000 g/mol, as measured by $^1$H NMR, assuming one olefin unsaturation per chain (preferably 500 to 15,000, preferably 700 to 10,000, preferably 800 to 8,000 g/mol, preferably 900 to 7,000, preferably 1000 to 6,000, preferably 1000 to 5,000);
  iii) an isobutyl chain end to allylic vinyl group ratio of 0.8:1 to 1.3:1.0;
  iv) less than 1400 ppm aluminum, (preferably less than 1200 ppm, preferably less than 1000 ppm, preferably less than 500 ppm, preferably less than 100 ppm).

In some embodiments of the above methods, $R_{11}$ can comprise a propylene copolymer having an Mn of 300 to 30,000 g/mol as measured by 1H NMR and assuming one olefin unsaturation per chain (preferably 400 to 20,000, preferably 500 to 15,000, preferably 600 to 12,000, preferably 800 to 10,000, preferably 900 to 8,000, preferably 900 to 7,000 g/mol), comprising 10 to 90 mol % propylene (preferably 15 to 85 mol %, preferably 20 to 80 mol %, preferably 30 to 75 mol %, preferably 50 to 90 mol %) and 10 to 90 mol % (preferably 85 to 15 mol %, preferably 20 to 80 mol %, preferably 25 to 70 mol %, preferably 10 to 50 mol %) of one or more alpha-olefin comonomers (preferably ethylene, butene, hexene, or octene, or decene, preferably ethylene), wherein the polymer has at least X % allyl chain ends (relative to total unsaturations), where X is 80% or more, preferably 85% or more, preferably 90% or more, preferably 95% or more. Alternatively, $R_{11}$ can have at least 80% isobutyl chain ends (based upon the sum of isobutyl and n-propyl saturated chain ends), preferably at least 85% isobutyl chain ends, preferably at least 90% isobutyl chain ends. Alternately, $R_{11}$ can have an isobutyl chain end to allylic vinyl group ratio of 0.8:1 to 1.35:1.0, preferably 0.9:1 to 1.20:1.0, preferably 0.9:1.0 to 1.1:1.0.

In other embodiments, $R_{11}$ can comprise a polypropylene copolymer having more than 90 mol % propylene (preferably 95 to 99 mol %, preferably 98 to 9 mol %) and less than 10 mol % ethylene (preferably 1 to 4 mol %, preferably 1 to 2 mol %), wherein the copolymer has:
  at least 93% allyl chain ends (preferably at least 95%, preferably at least 97%, preferably at least 98%);
  a number average molecular weight (Mn) of about 400 to about 30,000 g/mol, as measured by $^1$H NMR and assuming one olefin unsaturation per chain (preferably 500 to 20,000, preferably 600 to 15,000, preferably 700 to 10,000 g/mol, preferably 800 to 9,000, preferably 900 to 8,000, preferably 1000 to 6,000);
  an isobutyl chain end to allylic vinyl group ratio of 0.8:1 to 1.35:1.0, and
  less than 1400 ppm aluminum, (preferably less than 1200 ppm, preferably less than 1000 ppm, preferably less than 500 ppm, preferably less than 100 ppm).

In alternative embodiments, $R_{11}$ can comprise a polypropylene copolymer comprising:
  at least 50 (preferably 60 to 90, preferably 70 to 90) mol % propylene and from 10 to 50 (preferably 10 to 40, preferably 10 to 30) mol % ethylene, wherein the polymer has:
  at least 90% allyl chain ends (preferably at least 91%, preferably at least 93%, preferably at least 95%, preferably at least 98%);
  an Mn of about 150 to about 20,000 g/mol, as measured by $^1$H NMR and assuming one olefin unsaturation per chain (preferably 200 to 15,000, preferably 250 to 15,000, preferably 300 to 10,000, preferably 400 to 9,500, preferably 500 to 9,000, preferably 750 to 9,000); and
  an isobutyl chain end to allylic vinyl group ratio of 0.8:1 to 1.3:1.0, wherein monomers having four or more carbon atoms are present at from 0 to 3 mol % (preferably at less than 1 mol %, preferably less than 0.5 mol %, preferably at 0 mol %).

In further embodiments, $R_{11}$ can comprise a polypropylene copolymer comprising:
  at least 50 (preferably at least 60, preferably 70 to 99.5, preferably 80 to 99, preferably 90 to 98.5) mol % propylene, from 0.1 to 45 (preferably at least 35, preferably 0.5 to 30, preferably 1 to 20, preferably 1.5 to 10) mol % ethylene, and from 0.1 to 5 (preferably 0.5 to 3, preferably 0.5 to 1) mol % $C_4$ to $C_{12}$ olefin (such as butene, hexene or octene, or decene, preferably butene), wherein the polymer has:
  at least 90% allyl chain ends (preferably at least 91%, preferably at least 93%, preferably at least 95%, preferably at least 98%);

a number average molecular weight (Mn) of about 150 to about 15,000 g/mol, as measured by $^1$H NMR and assuming one olefin unsaturation per chain (preferably 200 to 12,000, preferably 250 to 10,000, preferably 300 to 10,000, preferably 400 to 9500, preferably 500 to 9,000, preferably 750 to 9,000); and an isobutyl chain end to allylic vinyl group ratio of 0.8:1 to 1.35:1.0.

In certain embodiments, $R_{11}$ can comprise a polypropylene copolymer comprising:

at least 50 (preferably at least 60, preferably 70 to 99.5, preferably 80 to 99, preferably 90 to 98.5) mol % propylene, from 0.1 to 45 (preferably at least 35, preferably 0.5 to 30, preferably 1 to 20, preferably 1.5 to 10) mol % ethylene, and from 0.1 to 5 (preferably 0.5 to 3, preferably 0.5 to 1) mol % diene (such as $C_4$ to $C_{12}$ alpha-omega dienes (such as butadiene, hexadiene, octadiene), norbornene, ethylidene norbornene, vinylnorbornene, norbornadiene, and dicyclopentadiene), wherein the polymer has:

at least 90% allyl chain ends (preferably at least 91%, preferably at least 93%, preferably at least 95%, preferably at least 98%);

a number average molecular weight (Mn) of about 150 to about 20,000 g/mol, as measured by $^1$H NMR and assuming one olefin unsaturation per chain (preferably 200 to 15,000, preferably 250 to 12,000, preferably 300 to 10,000, preferably 400 to 9,500, preferably 500 to 9,000, preferably 750 to 9,000); and an isobutyl chain end to allylic vinyl group ratio of 0.7:1 to 1.35:1.0.

In other embodiments of the above methods, $R_{11}$ can comprise poly(higher alpha-olefin) or polypropylene-co-higher alpha-olefin), the higher alpha-olefin including two or more carbon atoms on each side chain. For example, suitable higher alpha-olefins can include, but are not limited to, 1-butene, 1-pentene, 1-hexene, 1-heptene, 1-octene, 1-nonene, 1-decene, 1-undecene, 1-dodecene, 1-tridecene, 1-tetradecene, 1-hexadecene, 1-octadecene and the like.

In certain embodiments, $R_{11}$ includes those vinyl terminated macromonomers disclosed in U.S. Patent Application Publication Nos. 20120245312, 20120245310, 20120245311, 20120245313, and U.S. Provisional Application No. 61/704,604, the disclosure of each of which is incorporated by reference in its entirety herein.

In the disclosed method of preparation of compound of Formula B, maleic anhydride can be used for the reaction of converting a polymer base unit $R_{11}$ having a terminal vinyl functionality to a compound of Formula II. The reaction between $R_{11}$ and maleic anhydride can be initiated by a peroxide initiator which provides a radical species. The reaction under this condition can result in Formula II noted above, as illustrated below in Scheme 7:

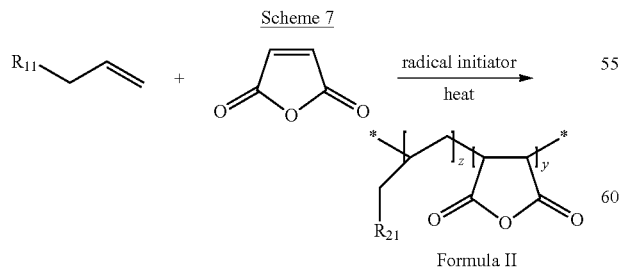

The vinyl-terminated polymer and maleic anhydride can be mixed either neat or in an inert solvent (e.g., paraffinic solvent, naphthenic solvent, aromatic solvent, halogenated solvent, mineral oil, synthetic fluid, etc.) with appropriate boiling point or boiling point range. The reaction can be conducted in an open system under atmospheric pressure by using standard laboratory glassware or in a closed system by using an autoclave (or any sealed vessel suitable for holding the pressure). The temperature can vary from 80 to 180° C., or preferably from 100 to 170° C., or preferably from 120 to 170° C., or preferably from 130 to 170° C. Reactant charge ratio of vinyl-terminated polymer to maleic anhydride can vary from about 1:1 to about 1:4, or from about 1:1 to about 1:3, or from about 1:1 to about 1:2, or from about 1:1 to about 1:1.5, or from about 1:1 to about 1:1.2. Suitable radical initiators include, but not limited to, organic peroxides such as di-tert-butyl peroxide, dicumyl peroxide, lauroyl peroxide, benzoyl peroxide, tert-butyl hydroperoxide, cumene hydroperoxide, tert-butyl peroxybenzoate (peroxy ester), tert-butyl peracetate (peroxy ester), 2,2'-azobisisobutyronitrile (AIBN), 1,1'-azobis(cyclohexanecarbonitrile) or similar diazo compounds. The radical initiator can be introduced in portions over a convenient period of time, if desired for controlling reaction rate, to the mixture of vinyl-terminated polymer and maleic anhydride at a suitable temperature (e.g., from about 120 to 165° C. for di-tert-butyl peroxide) needed for thermal decomposition of the radical initiator to generate radical species at a rate suitable for the reaction.

As previously noted, the method of preparing the compounds can include reacting the succinic anhydride-containing polymers obtained above with a polyamine. The reaction can proceed through a condensation mechanism. The polyamine can include linear, branched or cyclic isomers of an oligomer of ethyleneamine, or mixtures thereof, wherein each two neighboring nitrogens in the oligomer of ethyleneamine are bridged by one or two ethyleneamine groups. For example, the polyamine can be selected from polyethyleneamines with general molecular formula $H_2N(CH_2CH_2NH)_xH$ (where x=1, 2, 3, . . . ) such as ethylenediamine, diethylenetriamine, triethylenetetramine, tetraethylenepentamine, pentaethylenehexamine, hexaethyleneheptamine, and mixtures thereof. In some embodiments, the polyamine can comprise a heavy polyamine, such as polyethyleneamine heavy bottoms available from Dow Chemical as "Heavy Polyamine X" or HPA-X.

Using a reaction between the products of Scheme 7 and tetraethylenepentamine as an exemplary polyamine, the condensation reaction can be illustrated below in Scheme 8.

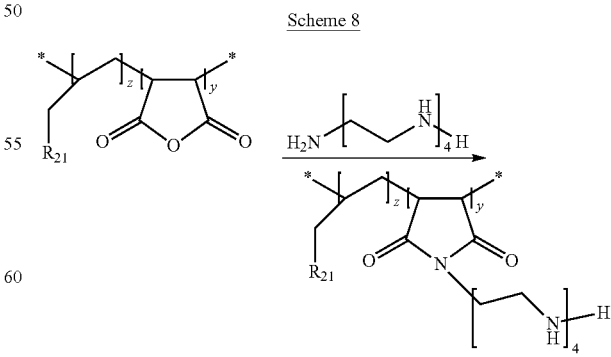

In alternative embodiments, nucleophilic reagents other than polyamines can be used to functionalize the compounds of Formula II. These reagents include, for example, monoamines, diamines, amino alcohols, polyetheramines, polyols, polyalkylene glycols, polyalkylene polyamine and the like.

Furthermore, vinylidene-terminated polymer or copolymer (e.g., ethylene-propylene copolymer, and propylene-higher alpha-olefin copolymer) can also be used as $R_{11}$. Illustrations for using vinylidene-terminated polypropylene and vinylidene-terminated propylene-higher alpha-olefin copolymer as $R_{11}$ are shown below in Scheme 9 and Scheme 10, respectively.

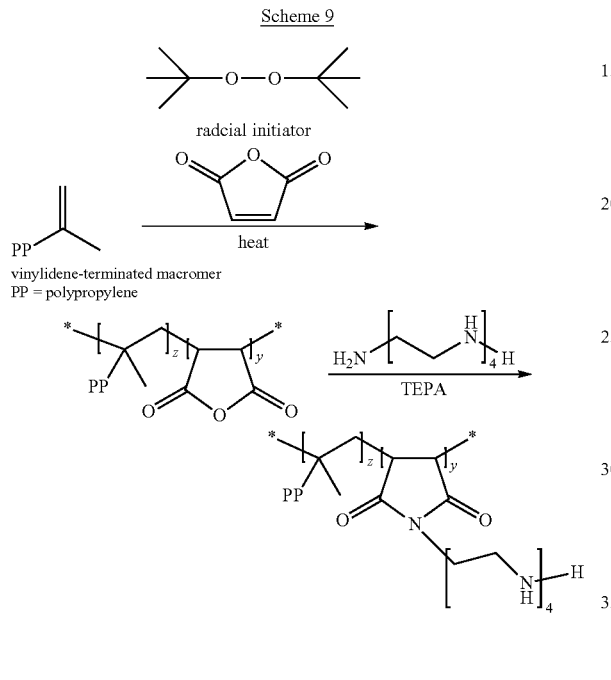

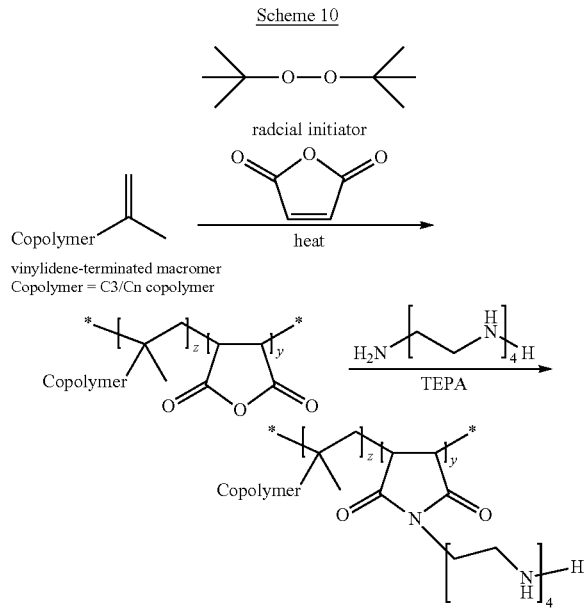

As a result of the amination reactions, the number of polymer chain attached to each polyamine molecule can vary from one to two to three or more. In addition, both primary and secondary amino groups on the polyamine can participate in the reaction with the anhydride-functionalized polymer. Other commercially available lower or higher polyamines with linear, branched, cyclic or heterocyclic structures can also be used. It is well-known and understood by those skilled in the art that these polyamines can be mixtures of compounds comprised of molecules with a distribution of chain lengths, different level and type of amine (primary, secondary, and tertiary) functional groups, and varying degree of linear, branched and cyclic structures. For example, possible isomers for tetraethylenepentamine include the following:

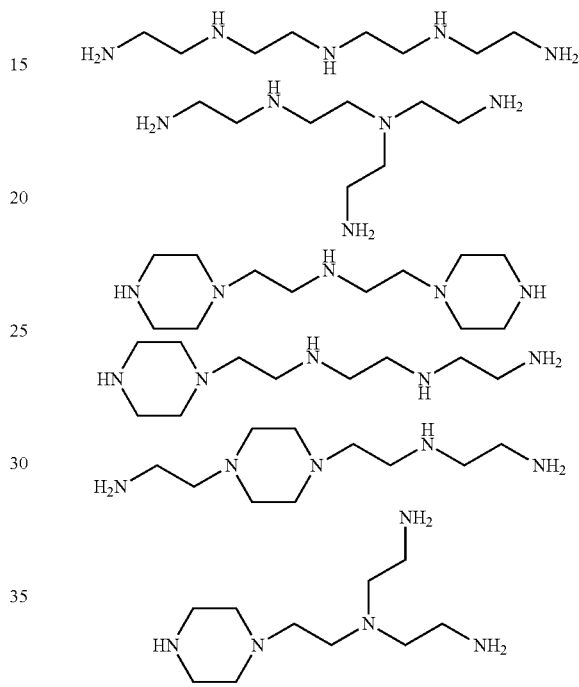

As the molecular weight of polyamines increases, the number of possible isomers increases as well.

In another aspect of the disclosed subject matter, compounds (additives) prepared by the method discussed above and various embodiments thereof are provided.

In another aspect, a method for reducing fouling in a hydrocarbon refining process is provided, which comprises providing a crude hydrocarbon for a refining process, and adding to the crude hydrocarbon an additive of Formula A or Formula B or various embodiments thereof as described above (e.g., at standard operation conditions).

Another aspect of the disclosed subject matter provides a system for refining hydrocarbons that includes at least one crude hydrocarbon refinery component, in which the crude hydrocarbon refinery component includes an additive selected from any one of the additives described herein. The crude hydrocarbon refining component can be selected from a heat exchanger, a furnace, a crude preheater, a coker preheater, a FCC slurry bottom, a debutanizer exchanger, a debutanizer tower, a feed/effluent exchanger, a furnace air preheater, a flare compressor component, a steam cracker, a steam reformer, a distillation column, a fractionation column, a scrubber, a reactor, a liquid-jacketed tank, a pipestill, a coker, and a visbreaker. For example, the crude hydrocarbon refining component can be a heat exchanger (e.g., a crude pre-heat train heat exchanger). Such methods and systems are described in greater details in the following sections and examples.

Another aspect of the disclosed subject matter provides a composition for reducing fouling that includes at least one of any of the above-described additives, and a boronating agent. The boronating agent can be any one or more compounds selected from boric acid, an ortho-borate, or a meta-borate, for example, boric acid, trimethyl metaborate (trimethoxyboroxine), triethyl metaborate, tributyl metaborate, trimethyl borate, triethylborate, triisopropyl borate (triisopropoxyborane), tributyl borate (tributoxyborane) and tri-t-butyl borate. Other boronating agents can be used, such as those disclosed in co-pending applications US20100038290 and US20100170829, each incorporated by reference herein in its entirety.

As disclosed in U.S. Patent Publication No. 20100170829, incorporated herein by reference in its entirety, monosuccinic anhydride compounds which are also suitable for use as antifouling additives can be formed by the methods described above, or, with reference to the method of synthesizing Formula A, by providing heat and not a radical initiator during the reaction of the polymer base unit and the anhydride.

Further Compositions for Reducing Fouling

The additives of the disclosed subject matter can be used in compositions that prevent fouling, including particulate-induced fouling. In addition to the additives of the disclosed subject matter, the compositions can further contain a hydrophobic oil solubilizer for the additive and/or a dispersant for the additive.

Suitable solubilizers can include, for example, surfactants, carboxylic acid solubilizers, such as the nitrogen-containing phosphorous-free carboxylic solubilizers disclosed in U.S. Pat. No. 4,368,133, hereby incorporated by reference in its entirety.

Also as disclosed in U.S. Pat. No. 4,368,133, hereby incorporated by reference in its entirety, surfactants that can be included in compositions of the disclosed subject matter can include, for example, cationic, anionic, nonionic or amphoteric type of surfactant. See, for example, McCutcheon's "Detergents and Emulsifiers", 1978, North American Edition, published by McCutcheon's Division, MC Publishing Corporation, Glen Rock, N.J., U.S.A., including pages 17-33, which is hereby incorporated by reference in its entirety.

The compositions of the disclosed subject matter can further include, for example, viscosity index improvers, anti-foamants, antiwear agents, demulsifiers, anti-oxidants, and other corrosion inhibitors.

Furthermore, the additives of the disclosed subject matter can be added with other compatible components that address other problems that can present themselves in an oil refining process known to one of ordinary skill in the art.

Uses of the Additives and Compositions for Antifouling Applications

The additives of the disclosed subject matter are generally soluble in a typical hydrocarbon refinery stream and can thus be added directly to the process stream, alone or in combination with other additives that either reduce fouling or improve some other process parameter.

The additives can be introduced, for example, upstream from the particular crude hydrocarbon refinery component(s) (e.g., a heat exchanger) in which it is desired to prevent fouling (e.g. particulate-induced fouling). Alternatively, the additive can be added to the crude oil prior to being introduced to the refining process, or at the very beginning of the refining process.

It is noted that water can have a negative impact on boron-containing additives. Accordingly, it is advisable to add boron-containing additives at process locations that have a minimal amount of water.

While not limited thereto, the additives of the disclosed subject matter are particularly suitable in reducing or preventing particulate-induced fouling. Thus one aspect of the disclosed subject matter provides a method of reducing and/or preventing, in particular, particulate-induced fouling that includes adding at least one additive of the disclosed subject matter to a process stream that is known, or believed to contribute to, particulate-induced fouling. To facilitate determination of proper injection points, measurements can be taken to ascertain the particulate level in the process stream. Thus, one embodiment of the disclosed subject matter includes identifying particular areas of a refining process that have relatively high particulate levels, and adding any one of the additives of the disclosed subject matter in close proximity to these areas (e.g., just upstream to the area identified as having high particulate levels).

In some embodiments of the disclosed subject matter, a method to reduce fouling is provided comprising adding any one of the above-mentioned additives or compositions to a crude hydrocarbon refinery component that is in fluid communication with a process stream that contains, at least 50 wppm of particulates, including organic and inorganic particulates. In another embodiment of the disclosed subject matter, a method to reduce fouling is provided comprising adding any one of the above-mentioned antifouling additives or compositions to a crude hydrocarbon refinery component that is in fluid communication with a process stream. In another embodiment of the disclosed subject matter, a method to reduce fouling is provided comprising adding any one of the above-mentioned additives to a crude hydrocarbon refinery component that is in fluid communication with a process stream that contains at least 250 wppm (or 1000 wppm, or 10,000 wppm) of particulates, including organic and inorganic particulates, as defined above.

In some embodiments of the disclosed subject matter, the additives or compositions of the disclosed subject matter are added to selected crude oil process streams known to contain, or possibly contain, problematic amounts of organic or inorganic particulate matter (e.g. 1-10,000 wppm), such as inorganic salts. Accordingly, the additives of the disclosed subject matter can be introduced far upstream, where the stream is relatively unrefined (e.g. the refinery crude pre-heat train). The additives can be also added, for example, after the desalter to counteract the effects of incomplete salt removal or to the bottoms exit stream from the fractionation column to counteract the high temperatures that are conducive to fouling.

FIG. 1 demonstrates possible additive injection points within the refinery crude pre-heat train for the additives of the disclosed subject matter, wherein the numbered circles represent heat exchangers. As shown in FIG. 1, the additives can be introduced in crude storage tanks and at several locations in the preheat train. This includes at the crude charge pump (at the very beginning of the crude pre-heat train), and/or before and after the desalter, and/or to the bottoms stream from a flash drum.

The total amount of additive to be added to the process stream can be determined by a person of ordinary skill in the art. In one embodiment, up to about 1000 wppm of additive is added to the process stream. For example, the additive can be added such that its concentration, upon addition, is about 50 ppm, 250 ppm or 500 ppm. More or less additive can be added depending on, for example, the amount of particulate in the stream, the ΔT associated with the particular process and the degree of fouling reduction desired in view of the cost of the additive.

The additives or compositions of the disclosed subject matter can be added in a solid (e.g. powder or granules) or liquid form directly to the process stream. As mentioned above, the additives or compositions can be added alone, or combined with other components to form a composition for reducing fouling (e.g. particulate-induced fouling). Any suitable technique can be used for adding the additive to the process stream, as known by a person of ordinary skill in the art in view of the process to which it is employed. As a non-limiting example, the additives or compositions can be introduced via injection that allows for sufficient mixing of the additive and the process stream.

* * *

EXAMPLES

The disclosed subject matter is further described by means of the examples, presented below. The use of such examples is illustrative only and in no way limits the scope and meaning of the disclosed subject matter or of any exemplified term. Likewise, the disclosed subject matter is not limited to any particular preferred embodiments described herein. Indeed, many modifications and variations of the disclosed embodiments will be apparent to those skilled in the art upon reading this specification.

Example 1

Synthesis of Compounds

Various examples of using the methods of compound synthesis described above are provided herein. Polyisobutylene succinimide dispersants were obtained from commercial suppliers (Infineum, Lubrizol, Chevron Oronite, Afton Chemical, BASF, etc). Alternatively, polyisobutylene-based polyamine succinimide dispersants were prepared by using commercially available highly reactive polyisobutylenes (HR-PIB) from BASF and from Texas Petrochemcials (TPC) as exemplified below.

Example 1A

Maleation of Vinylidene-Terminated Polyisobutylene (PIB) with Maleic Anhydride To a 300 ml stainless steel autoclave equipped with a mechanical stirrer and an $N_2$ inlet and an $N_2$ outlet was added highly reactive polyisobutylene (BASF Glissopal 2300, 85 g) followed by maleic anhydride (15.65 g, 159.6 mmol) at room temperature. The mixture was stirred and flushed three times with nitrogen at room temperature and pressurized to 80 psi. The mixture was heated to 250° C. for 2 hours and allowed to cool to room temperature. The pressure was released slowly and the autoclave was opened. The mixture was diluted with hexanes, filtered under house vacuum and the filtrate was concentrated on a rotary evaporator. The mixture was heated at 95° C. under high vacuum to afford a viscous light brown oily product (90.66 g). Elemental analyses for this PIB-SA material found C: 82.44%, H: 13.25%. The oxygen content of this material is estimated to be about 4.31 wt % by difference. The anhydride content of this polymer material is estimated to be about 0.898 mmol/g. Based on the molecular weight of polymer starting material, there is an average of 2.10 succinic anhydride functionality per polymer chain.

Example 1B

Maleation of Vinyl-Terminated Polypropylene (Vt-PP) with Maleic Anhydride

A mixture of vinyl-terminated polypropylene ($^1$H NMR Mn 1210 g/mol, 44.00 g) and maleic anhydride (10.70 g, 109.1 mmol) was heated at 205° C. for 24 hours under a nitrogen atmosphere. The mixture was cooled to room temperature, diluted with hexanes, filtered and concentrated on a rotary evaporator. Excess maleic anhydride was removed by heating under high vacuum to afford a viscous brown oily product (46.59 g). Elemental analyses for this PP-SA material found C: 81.27%, H: 13.19%. The oxygen content of this material is estimated to be about 5.54 wt % by difference. The anhydride content of this polymer material is estimated to be about 1.154 mmol/g. Based on the molecular weight of polymer starting material, there is an average of 1.55 succinic anhydride functionality per polymer chain.

Example 1C

Maleation of Vinyl-Terminated Propylene/1-Hexene Copolymer with Maleic Anhydride A mixture of vinyl-terminated propylene/1-hexene copolymer ($^1$H NMR Mn 1638 g/mol, 48.60 g) and maleic anhydride (11.64 g, 118.7 mmol) was heated at 190° C. for 42 hours under a nitrogen atmosphere. The mixture was cooled to room temperature, diluted with hexanes, filtered and concentrated on a rotary evaporator. Excess maleic anhydride was removed by heating under high vacuum to afford a viscous brown oily product (53.10 g). Elemental analyses for this $C_3C_6$-SA material found C: 82.33%, H: 13.26%. The oxygen content of this material is estimated to be about 4.41 wt % by difference. The anhydride content of this polymer material is estimated to be about 0.919 mmol/g. Based on the molecular weight of polymer starting material, there is an average of 1.66 succinic anhydride functionality per polymer chain.

Example 1D

Condensation of Polyisobutylene Succinic Anhydride (PIB-SA) with Tetraethylenepentamine (TEPA)

A mixture of polyisobutylene succinic anhydride from Example 1A (25.00 g, 22.45 mmol anhydride) and xylenes (100 ml) was stirred at room temperature under a nitrogen atmosphere and a solution of tetraethylenepentamine (2.36 g, 12.47 mmol) in xylenes (15 ml) was slowly added. The resulting mixture was heated in an oil bath at 165° C. for 15.5 hours. The brown mixture was cooled to room temperature and excess xylenes removed on a rotary evaporator. The residual liquid product was further purified by heating under high vacuum to afford a viscous brown oily product (26.91 g). Elemental analyses for this PIB-SA-TEPA compound found C: 81.32%, H: 13.25%, N: 3.05%.

Example 1E

Condensation of Polypropylene Succinic Anhydride (PP-SA) with Tetraethylenepentamine (TEPA)

A mixture of polypropylene succinic anhydride from Example 1B (18.00 g, 20.77 mmol anhydride) and xylenes (50 ml) was stirred at room temperature under a nitrogen atmosphere and a solution of tetraethylenepentamine (3.15 g, 16.6 mmol) in xylenes (10 ml) was slowly added. The resulting mixture was heated in an oil bath at 175° C. for 24 hours. The brown mixture was cooled to room temperature and excess xylenes removed on a rotary evaporator. The residual liquid product was further purified by heating under high vacuum to afford a viscous brown oily product (20.52 g). Elemental analyses for this PP-SA-TEPA material found C: 78.30%, H: 12.97%, N: 5.11%.

Example 1F

Condensation of Propylene/1-Hexene Succinic Anhydride ($C_3C_6$-SA) with Tetraethylenepentamine (TEPA)

A mixture of propylene/1-hexene succinic anhydride Example 1C (25.70 g, 23.62 mmol anhydride) and xylenes (60 ml) was stirred at room temperature under a nitrogen atmosphere and a solution of tetraethylenepentamine (2.55 g, 13.5 mmol) in xylenes (15 ml) was slowly added. The resulting mixture was heated in an oil bath at 170° C. for 24 hours. The brown mixture was cooled to room temperature and excess xylenes removed on a rotary evaporator. The residual liquid product was further purified by heating under high vacuum to afford a viscous brown oily product (27.58 g). Elemental analyses for this $C_3C_6$-SA-TEPA material found C: 81.38%, H: 12.74%, N: 3.30%.

Example 1G

Maleation of Vinyl-Terminated Atactic Polypropylene

To a two-neck 500 ml round-bottomed flask equipped with an $N_2$ inlet and an $N_2$ outlet was added vinyl-terminated atactic polypropylene (GPC $M_w$ 5646, $M_n$ 1474, $^1$H NMR Mn 1190.19 g/mol, 75.00 g, 63.02 mmol) followed by maleic anhydride (15.45 g, 157.56 mmol) at room temperature. The mixture was flushed with nitrogen for 10 min at room temperature and the mixture was heated to 190° C. (oil bath) for 63.5 hours under a nitrogen atmosphere. Additional maleic anhydride (3.10 g, 31.61 mmol) was added to the mixture that had been cooled to about 120° C. and heating was continued at 190° C. (oil bath) for an additional 17 hours under a nitrogen atmosphere. The mixture was cooled to room temperature, diluted with hexanes, filtered and concentrated on a rotary evaporator. Excess maleic anhydride was removed by heating at 95-100° C. under high vacuum to afford a light brown viscous oily product (85.70 g). GPC $M_w$ 4020, $M_n$ 1413. Elemental analyses for this polypropylene succinic anhydride found C: 80.79%, H: 12.51%. The oxygen content of this material is estimated to be about 6.70 wt % by difference. The anhydride content of this polymer material is estimated to be about 1.396 mmol/g. Based on the molecular weight of polymer starting material, there is an average of 1.93 succinic anhydride functionality per polymer chain.

Example 1H

Maleation of Vinyl-Terminated Atactic Polypropylene

To a 300 ml stainless steel autoclave equipped with a mechanical stirrer and an $N_2$ inlet and a $N_2$ outlet was added vinyl-terminated atactic polypropylene (GPC $M_w$ 2387, $M_n$ 1069, $^1$H NMR Mn 1015.76 g/mol, 90 g, 88.60 mmol) followed by maleic anhydride (34.75 g, 354.37 mmol) at room temperature. The mixture was stirred and flushed three times with nitrogen at room temperature and pressurized to about 250 psi with nitrogen. The mixture was heated to 250° C. for 3 hours at about 400 psi and allowed to cool to room temperature. The pressure was released slowly and the autoclave was opened. The mixture was diluted with hexanes, filtered under house vacuum and the filtrate was concentrated on a rotary evaporator. Excess maleic anhydride was removed by heating at 95° C. under high vacuum to afford a light brown viscous oily product (100.92 g). GPC $M_w$ 2527, $M_n$ 1112. Elemental analyses for this polypropylene succinic anhydride found C: 77.92%, H: 11.77%. The oxygen content of this material is estimated to be about 10.31 wt % by difference. The anhydride content of this copolymer material is estimated to be about 2.148 mmol/g. Based on the molecular weight of polymer starting material, there is an average of about 2.76 succinic anhydride functionality per polymer chain.

Example 1J

Maleation of Vinyl-Terminated Propylene/1-Hexene Copolymer

To a two-neck 500 ml round-bottomed flask equipped with an $N_2$ inlet and an $N_2$ outlet was added vinyl-terminated propylene/1-hexene copolymer (GPC $M_w$ 1259, $M_n$ 889, $^1$H NMR Mn 846.53 g/mol, 150 g, 177.19 mmol) followed by maleic anhydride (43.44 g, 442.99 mmol) at room temperature. The mixture was flushed with nitrogen for 10 min at room temperature and the mixture was heated to 190° C. (oil bath) for 38.5 hours under a nitrogen atmosphere. The mixture was cooled to room temperature, diluted with hexanes, filtered and concentrated on a rotary evaporator. Excess maleic anhydride was removed by heating at 95-100° C. under high vacuum to afford a light brown viscous oily product (178.94 g). GPC $M_w$ 1587, $M_n$ 1023. Elemental analyses for this propylene/1-hexene succinic anhydride copolymer found C: 80.01%, H: 12.15%. The oxygen content of this material is estimated to be about 7.84 wt % by difference. The anhydride content of this copolymer material is estimated to be about 1.633 mmol/g. Based on the molecular weight of polymer starting material, there is an average of about 1.65 succinic anhydride functionality per polymer chain.

Example 1K

Maleation of Vinyl-Terminated Propylene/1-Hexene Copolymer

To a 300 ml stainless steel autoclave equipped with a mechanical stirrer and an $N_2$ inlet and an $N_2$ outlet was added vinyl-terminated propylene/1-hexene copolymer (GPC $M_w$ 1894, $M_n$ 997, $^1$H NMR Mn 1012.79 g/mol, 90 g, 88.86 mmol) followed by maleic anhydride (20.91 g, 213.24 mmol) at room temperature. The mixture was stirred and flushed three times with nitrogen at room temperature and pressurized to about 80 psi with nitrogen. The mixture was heated to 250° C. for 3 hours at about 140 psi and allowed to cool to room temperature. The pressure was released slowly and the autoclave was opened. The mixture was diluted with hexanes, filtered under house vacuum and the filtrate was concentrated on a rotary evaporator. Excess maleic anhydride was removed by heating at 95° C. under high vacuum to afford a light brown viscous oily product (103.54 g). GPC $M_w$ 1937, $M_n$ 1058. Elemental analyses for this propylene/1-hexene succinic anhydride copolymer found C: 80.79%, H: 12.61%. The oxygen content of this material is estimated to be about 6.60 wt % by difference. The anhydride content of this copolymer material is estimated to be about 1.375 mmol/g. Based on the molecular weight of polymer starting material, there is an average of about 1.61 succinic anhydride functionality per polymer chain.

Example 1L

Maleation of Vinyl-Terminated Propylene/1-Butene Copolymer

To a two-neck 250 ml round-bottomed flask equipped with an $N_2$ inlet and an $N_2$ outlet was added vinyl-terminated propylene/1-butene copolymer (GPC $M_w$ 2197, $M_n$ 1030, $^1$H NMR Mn 1062.16 g/mol, 50 g, 47.07 mmol) followed by maleic anhydride (9.23 g, 94.13 mmol) at room temperature. The mixture was flushed with nitrogen for 10 min at room temperature and the mixture was heated to 190° C. (oil bath) for 84.5 hours under a nitrogen atmosphere. The mixture was cooled to room temperature, diluted with hexanes, filtered and concentrated on a rotary evaporator. Excess maleic anhydride was removed by heating at 95-100° C. under high vacuum to afford a light brown viscous oily product (54.97 g). The molecular weight of the product, $M_w$ 2294, $M_n$ 1242, determined by GPC. Elemental analyses for this propylene/1-butene succinic anhydride copolymer found C: 81.76%, H: 13.09%. The oxygen content of this material is estimated to be about 5.15 wt % by difference. The anhydride content of this copolymer material is estimated to be about 1.073 mmol/g. Based on the molecular weight of polymer starting material, there is an average of about 1.27 succinic anhydride functionality per polymer chain.

Example 1M

Condensation of Polypropylene Succinic Anhydride with Tetraethylenepentamine (DMA2)

A mixture of polypropylene succinic anhydride (28.00 g, from Example 1G, 39.09 mmol anhydride) and xylenes (85 ml) was stirred at room temperature under a nitrogen atmosphere and a solution of tetraethylenepentamine (4.11 g, 21.71 mmol) in xylenes (15 ml) was slowly added. The resulting mixture was heated in an oil bath at 170° C. for 24 hours under a nitrogen atmosphere and an azeotropic mixture of xylenes and water was collected in a Dean-Stark trap. The light brown mixture was cooled to room temperature and excess xylenes removed on a rotary evaporator. The residual liquid product was further purified by heating at 95° C. under high vacuum to afford a dark brown viscous product (28.21 g), whose $M_w$ was determined to be 4738 by GPC. Elemental analyses for this PP-SA-TEPA material found C: 79.04%, H: 12.46%, N: 5.07%.

Example 1N

Condensation of Propylene/1-Hexene Succinic Anhydride ($C_3C_6$-SA) with Tetraethylenepentamine (TEPA)

A mixture of propylene/1-hexene succinic anhydride (30.00 g, from Example 1J, 48.99 mmol anhydride) and xylenes (85 ml) was stirred at room temperature under a nitrogen atmosphere and a solution of tetraethylenepentamine (4.22 g, 22.29 mmol) in xylenes (15 ml) was slowly added. The resulting mixture was heated in an oil bath at 165° C. for 24 hours under a nitrogen atmosphere and an azeotropic mixture of xylenes and water was collected in a Dean-Stark trap. The light brown mixture was cooled to room temperature and excess xylenes removed on a rotary evaporator. The residual liquid product was further purified by heating at 95° C. under high vacuum to afford a brown viscous product (33.24 g), whose molecular weight $M_w$ was determined to be 4684 by GPC. Elemental analyses for this $C_3C_6$-SA-TEPA material found C: 77.96%, H: 12.11%, N: 4.46%.

Example 1P

Condensation of Propylene/1-Butene Succinic Anhydride ($C_3C_4$-SA) with Tetraethylenepentamine (TEPA)

A mixture of propylene/1-butene succinic anhydride (25.00 g, from Example 1L, 26.83 mmol anhydride) and xylenes (85 ml) was stirred at room temperature under a nitrogen atmosphere and a solution of tetraethylenepentamine (3.38 g, 17.86 mmol) in xylenes (15 ml) was slowly added. The resulting mixture was heated in an oil bath at 165° C. for 24 hours under a nitrogen atmosphere and an azeotropic mixture of xylenes and water was collected in a Dean-Stark trap. The light brown mixture was cooled to room temperature and excess xylenes removed on a rotary evaporator. The residual liquid product was further purified by heating at 95° C. under high vacuum to afford a dark brown viscous product (27.57 g), whose molecular weight $M_w$ was determined to be 3878 by GPC. Elemental analyses for this $C_3C_4$-SA-TEPA material found C: 79.71%, H: 13.04%, N: 4.31%.

Example 1Q

Copolymerization of Vinyl-Terminated Atactic Polypropylene with Maleic Anhydride A mixture of vinyl-terminated atactic polypropylene (NB#25136-002-001, GPC $M_w$ 2301, $M_n$ 1180, $^1$H NMR Mn 944.7 g/mol, 15.00 g, 15.88 mmol), maleic anhydride (2.49 g, 25.39 mmol) and xylenes (14 ml) was heated to 150° C. (oil bath temperature) under a nitrogen atmosphere. A solution of di-tert-butyl peroxide (0.244 g, 1.67 mmol) in xylenes (5 ml) was added slowly to the mixture over 1 hour while the oil bath was maintained at 150° C. After complete addition of the peroxide solution, the mixture was heated at 155° C. for 4.5 hours and then at 160° C. for 1 hour under a nitrogen atmosphere. The mixture was cooled to room temperature and excess solvent and volatile material were removed on a rotary evaporator. The crude product was further purified by heating at 95° C. under high vacuum to afford a light yellow viscous material (17.26 g). The conversion of polypropylene starting material was about 81% according to $^1$H NMR spectroscopy. The molecular weight of the material was determined to be M$_w$ 4247, M$_n$ 1977 (by GPC). Elemental analyses for this PP-MA copolymer material found C: 81.01%, H: 12.56%. The oxygen content of this material is estimated to be about 6.43 wt % by difference. The anhydride content of this polymer material is estimated to be about 1.340 mmol/g.

Example 1R

Copolymerization of Vinyl-Terminated Atactic Polypropylene with Maleic Anhydride A mixture of vinyl-terminated atactic polypropylene (GPC M$_w$ 4453, M$_n$ 2087, $^1$H NMR Mn 1751.5 g/mol, 30.00 g, 17.13 mmol), maleic anhydride (2.69 g, 27.43 mmol) and xylenes (17 ml) was heated to 148° C. (oil bath temperature) under a nitrogen atmosphere. A solution of di-tert-butyl peroxide (0.426 g, 2.91 mmol) in xylenes (5 ml) was added slowly to the mixture over 2 hours while the oil bath was maintained at 148° C. After complete addition of the peroxide solution, the mixture was heated at 148° C. for 4.5 hours under a nitrogen atmosphere. Additional di-tert-butyl peroxide (0.15 g, 1.03 mmol) in xylenes (5 ml) was added to the mixture and heating was continued at 148° C. for an additional 4.5 hours. A further additional amount of di-tert-butyl peroxide (0.15 g, 1.03 mmol) in xylenes (5 ml) was added to the mixture and heating was continued at 148° C. for an additional 3.5 hours. The mixture was cooled to room temperature and excess solvent and volatile material were removed on a rotary evaporator. The crude product was further purified by heating at 95° C. under high vacuum to afford a colorless viscous material (33.10 g). The conversion of polypropylene starting material was about 83% according to $^1$H NMR spectroscopy. The molecular weight of the material was determined as M$_w$ 6552, M$_n$ 2539 (by GPC). Elemental analyses for this PP-MA copolymer material found C: 82.89%, H: 13.10%. The oxygen content of this material is estimated to be about 4.01 wt % by difference. The anhydride content of this polymer material is estimated to be about 0.835 mmol/g.

Example 1S

Copolymerization of Vinyl-Terminated Propylene/1-Hexene Copolymer with Maleic Anhydride A mixture of vinyl-terminated propylene/1-hexene copolymer (GPC M$_w$ 3157, M$_n$ 1453, $^1$H NMR Mn 1567.2 g/mol, 30.00 g, 19.14 mmol), maleic anhydride (3.75 g, 38.24 mmol) and xylenes (18 ml) was heated to 163° C. (oil bath temperature) under a nitrogen atmosphere. A solution of di-tert-butyl peroxide (0.560 g, 3.83 mmol) in xylenes (8 ml) was added slowly to the mixture over 80 minutes while the oil bath was maintained at 163° C. After complete addition of the peroxide solution, the mixture was heated at 163° C. for 15.5 hours under a nitrogen atmosphere. The mixture was cooled to room temperature and excess solvent and volatile material were removed on a rotary evaporator. The crude product was further purified by heating at 95° C. under high vacuum to afford a light yellow viscous material (34.22 g). The conversion of propylene/1-hexene copolymer starting material was about 87% according to $^1$H NMR spectroscopy. Elemental analyses for this $C_3C_6$-MA copolymer material found C: 81.79%, H: 13.02%. The oxygen content of this material is estimated to be about 5.19 wt % by difference. The anhydride content of this polymer material is estimated to be about 1.081 mmol/g.

Example 1T

Functionalization of Polypropylene Maleic Anhydride Copolymer with Tetraethylenepentamine A mixture of polypropylene/maleic anhydride (PP-MA) copolymer (6.00 g, from Example 1Q, 8.04 mmol anhydride) and xylenes (45 ml) was stirred at room temperature under a nitrogen atmosphere and a solution of tetraethylenepentamine (1.17 g, 6.18 mmol) in xylenes (5 ml) was slowly added. The resulting mixture was heated in an oil bath at 170° C. for 72 hours under a nitrogen atmosphere and an azeotropic mixture of xylenes and water was collected in a Dean-Stark trap. The light brown mixture was cooled to room temperature and excess xylenes removed on a rotary evaporator. The residual product was further purified by heating at 95° C. under high vacuum to afford a light brown viscous product (6.92 g). The molecular weight of this product was determined as M$_w$ 4247, M$_n$ 1302 (by GPC). Elemental analyses for this PP-MA-TEPA copolymer additive found C: 78.00%, H: 12.43%, N: 5.70%.

Example 1U

Functionalization of Polypropylene-Maleic Anhydride Copolymer with Tetraethylenepentamine A mixture of polypropylene/maleic anhydride (PP-MA) copolymer (8.00 g, from Example 1R, 6.68 mmol anhydride) and xylenes (55 ml) was stirred at room temperature under a nitrogen atmosphere and a solution of tetraethylenepentamine (0.90 g, 4.75 mmol) in xylenes (5 ml) was slowly added. The resulting mixture was heated in an oil bath at 170° C. for 48 hours under a nitrogen atmosphere and an azeotropic mixture of xylenes and water was collected in a Dean-Stark trap. The light brown mixture was cooled to room temperature and excess xylenes removed on a rotary evaporator. The residual product was further purified by heating at 95° C. under high vacuum to afford a light brown viscous product (8.66 g), whose molecular weight Mw was determined to be 8440 by GPC. Elemental analyses for this PP-MA-TEPA copolymer additive found C: 80.47%, H: 12.92%, N: 3.62%.

Example 1V

Functionalization of Propylene/1-Hexene-Maleic Anhydride Copolymer with Triethylenetetramine A mixture of vinyl-terminated propylene/1-hexene-maleic anhydride ($C_3C_6$-MA) copolymer (8.00 g, from Example 1S, 8.65 mmol anhydride) and xylenes (55 ml) was stirred at room temperature under a nitrogen atmosphere and a solution of triethylenetetramine (0.903 g, 6.18 mmol) in xylenes (5 ml) was slowly added. The resulting mixture was heated in an oil bath at 165° C. for 24 hours under a nitrogen atmosphere and an azeotropic mixture of xylenes and water was collected in a Dean-Stark trap. The light brown mixture was cooled to room temperature and excess xylenes removed on a rotary evaporator. The residual product was further purified by heating at 95° C. under high vacuum to afford a light brown viscous product (8.70 g), whose molecular weight Mw was determined to be 5690 by GPC. Elemental analyses for this $C_3C_6$-MA-TEPA copolymer additive found C: 80.39%, H: 12.78%, N: 3.62%.

Example 2

Fouling Reduction Measured in the Alcor HLPS (Hot Liquid Process Simulator)

Figure 2:
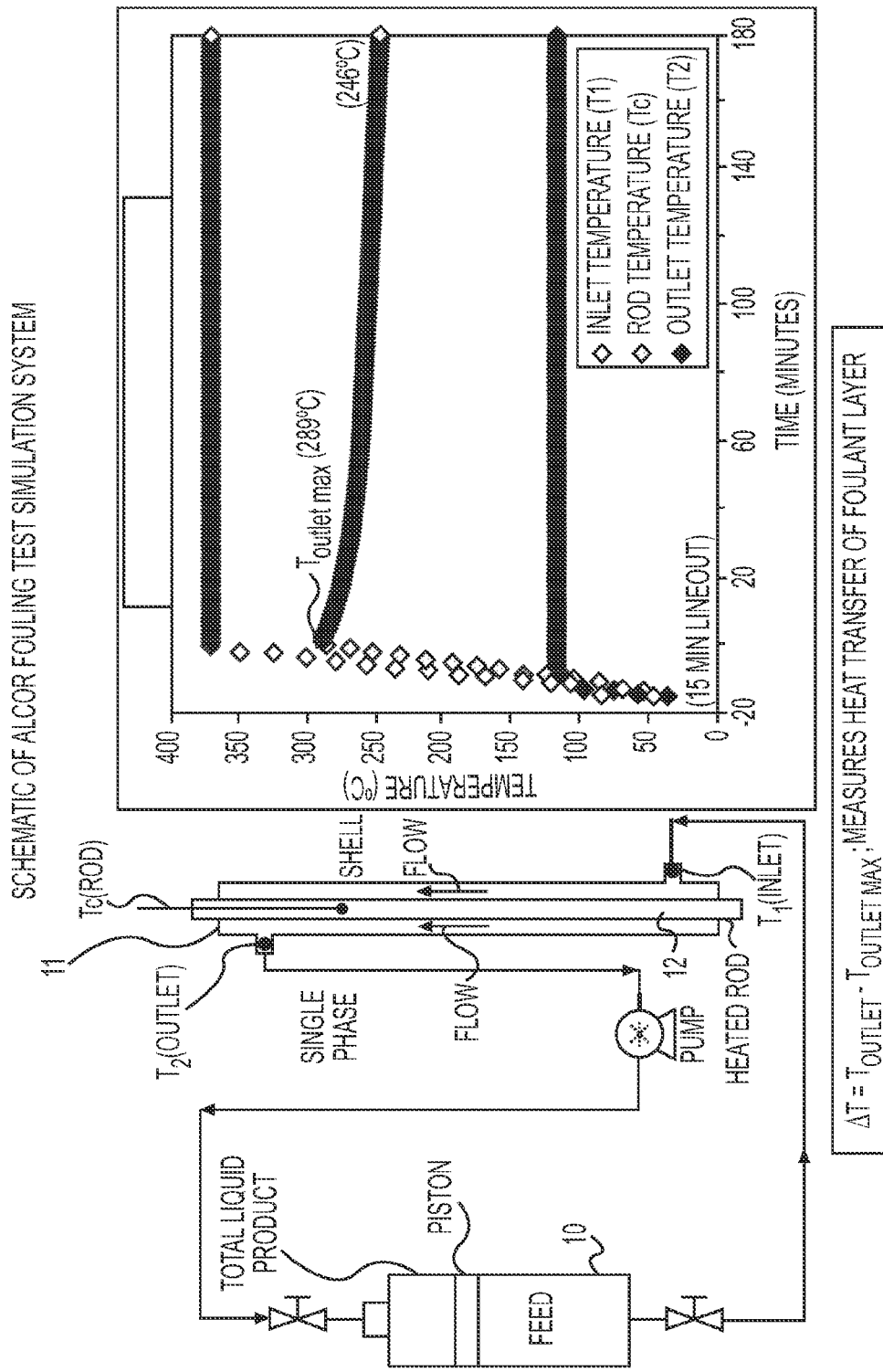
FIG. 2 is a schematic of the Alcor Hot Liquid Process Simulator (HLPS) employed in Example 3 of this application.

FIG. 2 depicts an Alcor HLPS (Hot Liquid Process Simulator) testing apparatus used to measure the impact of addition of particulates to a crude oil on fouling and the impact the addition of an additive of the disclosed subject matter has on the mitigation of fouling. The testing arrangement includes a reservoir 10 containing a feed supply of crude oil. The feed supply of crude oil can contain a base crude oil containing a whole crude or a blended crude containing two or more crude oils. The feed supply is heated to a temperature of approximately 150° C./302° F. and then fed into a shell 11 containing a vertically oriented heated rod 12. The heated rod 12 is formed from carbon-steel (1018). The heated rod 12 simulates a tube in a heat exchanger. The heated rod 12 is electrically heated to a surface temperature of 370° C./698° F. or 400° C./752° F. and maintained at such temperature during the trial. The feed supply is pumped across the heated rod 12 at a flow rate of approximately 3.0 mL/minute. The spent feed supply is collected in the top section of the reservoir 10. The spent feed supply is separated from the untreated feed supply oil by a sealed piston, thereby allowing for once-through operation. The system is pressurized with nitrogen (400-500 psig) to ensure gases remain dissolved in the oil during the test. Thermocouple readings are recorded for the bulk fluid inlet and outlet temperatures and for surface of the rod 12.

During the constant surface temperature testing, foulant deposits and builds up on the heated surface. The foulant deposits are thermally degraded to coke. The coke deposits cause an insulating effect that reduces the efficiency and/or ability of the surface to heat the oil passing over it. The resulting reduction in outlet bulk fluid temperature continues over time as fouling continues. This reduction in temperature is referred to as the outlet liquid $\Delta T$ or $\Delta T$ and can be dependent on the type of crude oil/blend, testing conditions and/or other effects, such as the presence of salts, sediment or other fouling promoting materials. A standard Alcor fouling test is carried out for 180 minutes. The total fouling, as measured by the total reduction in outlet liquid temperature over time, is plotted on the y-axis of FIGS. 5-11 and is the observed outlet temperature ($T_{outlet}$) minus the maximum observed outlet $T_{outlet\ max}$ (presumably achieved in the absence of any fouling).

Example 2A

Antifouling Additive 1 ("AFA1"), a commercially available preparation of polyisobutylene-succinic anhydride-polyamine (PIB-SA-PAM) was added to crude oil to a concentration of 374 ppm. 11 cc of water was then added to said mixture and blended for 10 seconds at 50% power using a Waring blender to generate a water-in-oil emulsion. 200 cc of said emulsion was placed into two separate Electrostatic Dehydration and Precipitation Tester (EDPT) transparent vessels (available from Inter AV Inc.) and a voltage of 3500 volts was applied to the emulsion at an interval of 2 minutes for a duration of 16 minutes at room temperature. 120 ml of the dehydrated crude was then added to 680 ml of the original crude oil with pre-added iron oxide and mixed well. The final concentration of iron oxide in the resulting crude oil blend is 200 wppm, and the final concentration of AFA1 is approximately 50 wppm. This crude blend containing AFA1 and iron oxide was subsequently evaluated for antifouling as described below and as illustrated in FIG. 3.

Figure 3:
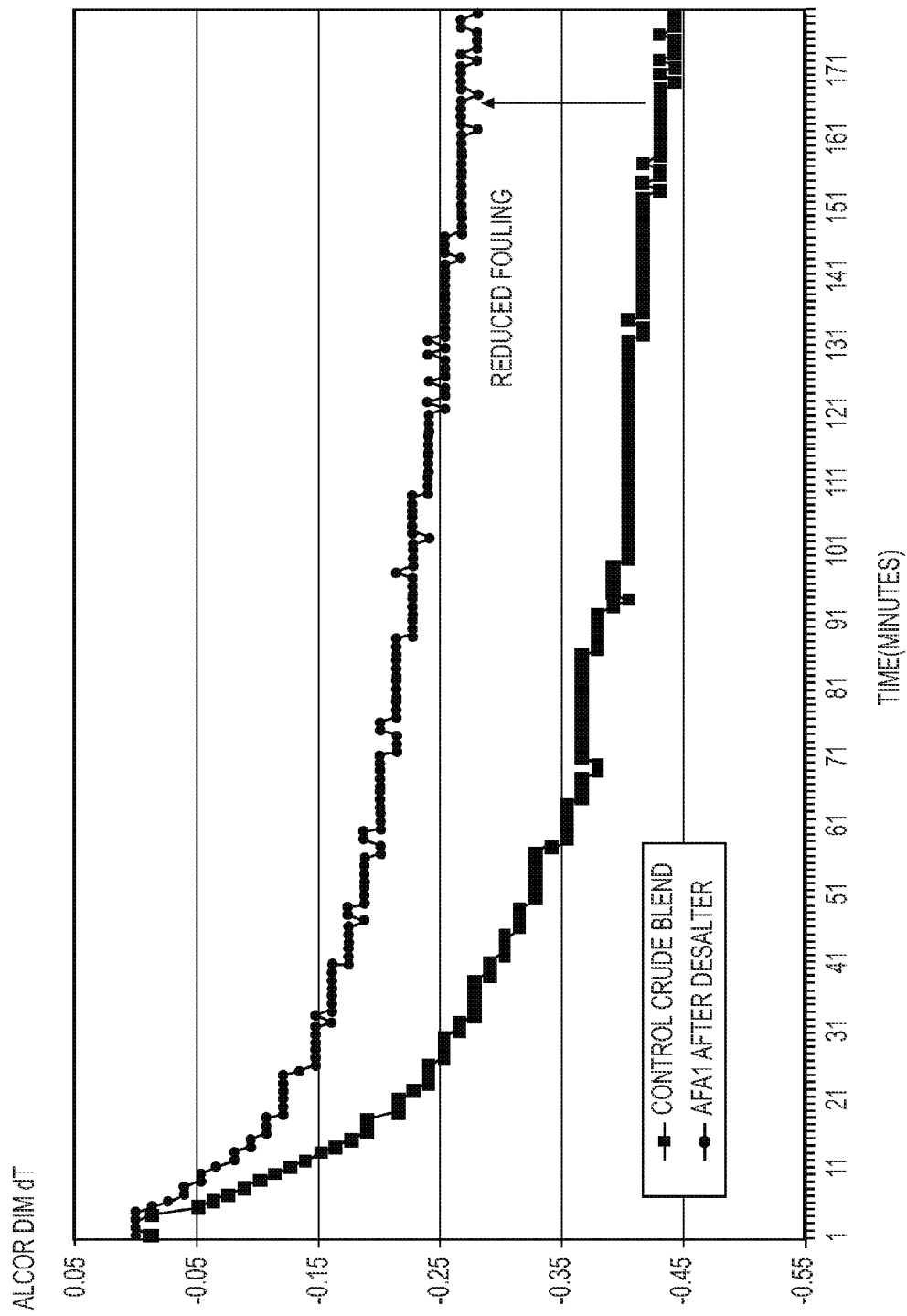
FIG. 3 is a graph demonstrating the effects of fouling of a control crude oil blend sample and a dehydrated crude oil blend sample treated with approximately 50 wppm of an additive according to the disclosed subject matter, as measured by the Alcor HLPS apparatus depicted in FIG. 2.

FIG. 3 illustrates the impact of fouling of a refinery component over 180 minutes. Two blends were tested in the Alcor unit: a crude oil control containing added rust (iron oxide) particles (200 wppm) without an additive, and the crude oil blend prepared as noted above containing 200 wppm of iron oxide and approximately 50 wppm AFA1. As FIG. 3 demonstrates, the reduction in the outlet temperature over time (due to fouling) is less for the process blend containing the additive AFA1 as compared to the crude oil control without the additive. This indicates that the additive remains in the crude during the dehydration and electrocoalescence processes and is able to effectively reduce fouling of a heat exchanger.

Example 2B

Antifouling Additive 2 ("AFA2"), polypropylene-succinic anhydride-polyamine (PP-SA-PAM) prepared according to Example 1E above, was added to crude oil to a concentration of 374 ppm. 11 cc of water was then added to said mixture and blended for 10 seconds at 50% power using a Waring blender to generate a water-in-oil emulsion. 200 cc of said emulsion was placed into two separate Electrostatic Dehydration and Precipitation Tester (EDPT) transparent vessels and a voltage of 3500 volts was applied to the emulsion at an interval of 2 minutes for a duration of 16 minutes at room temperature. 120 ml of the dehydrated crude was then added to 680 ml of the original crude oil with pre-added iron oxide and mixed well. The final concentration of iron oxide in the resulting crude oil blend is 200 wppm, and the final concentration of AFA2 is approximately 50 wppm. It was assumed that the antifouling additive localized to the crude phase and was not degraded during dehydration. This crude blend containing AFA2 and iron oxide was subsequently evaluated for antifouling as described below and as illustrated in FIG. 4.

Figure 4:
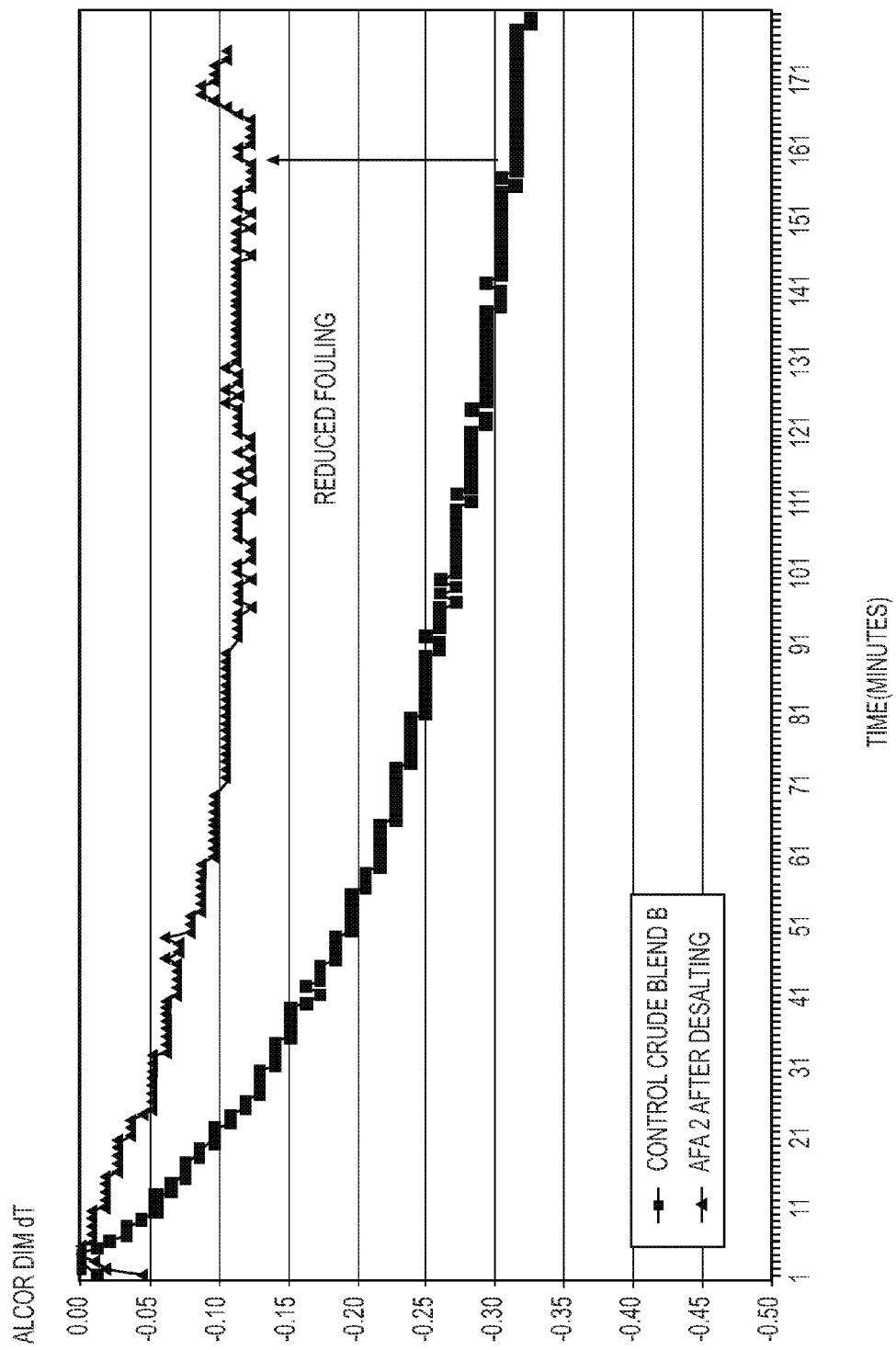
FIG. 4 is a graph demonstrating the effects of fouling of a control crude oil blend sample and a dehydrated crude oil blend sample treated with approximately 50 wppm of an additive according to the disclosed subject matter, as measured by the Alcor HLPS apparatus depicted in FIG. 2.

FIG. 4 illustrates the impact of fouling of a refinery component over 180 minutes. Two blends were tested in the Alcor unit: a crude oil control containing 200 wppm of added rust (iron oxide) particles without an additive, and the crude oil blend prepared above containing 200 wppm of iron oxide and approximately 50 wppm AFA2. As FIG. 4 demonstrates, the reduction in the outlet temperature over time (due to fouling) is less for the process blend containing the additive AFA2 as compared to the crude oil control without the additive. This indicates that the additive is effective at reducing fouling of a heat exchanger.

Example 2C

Figure 5:
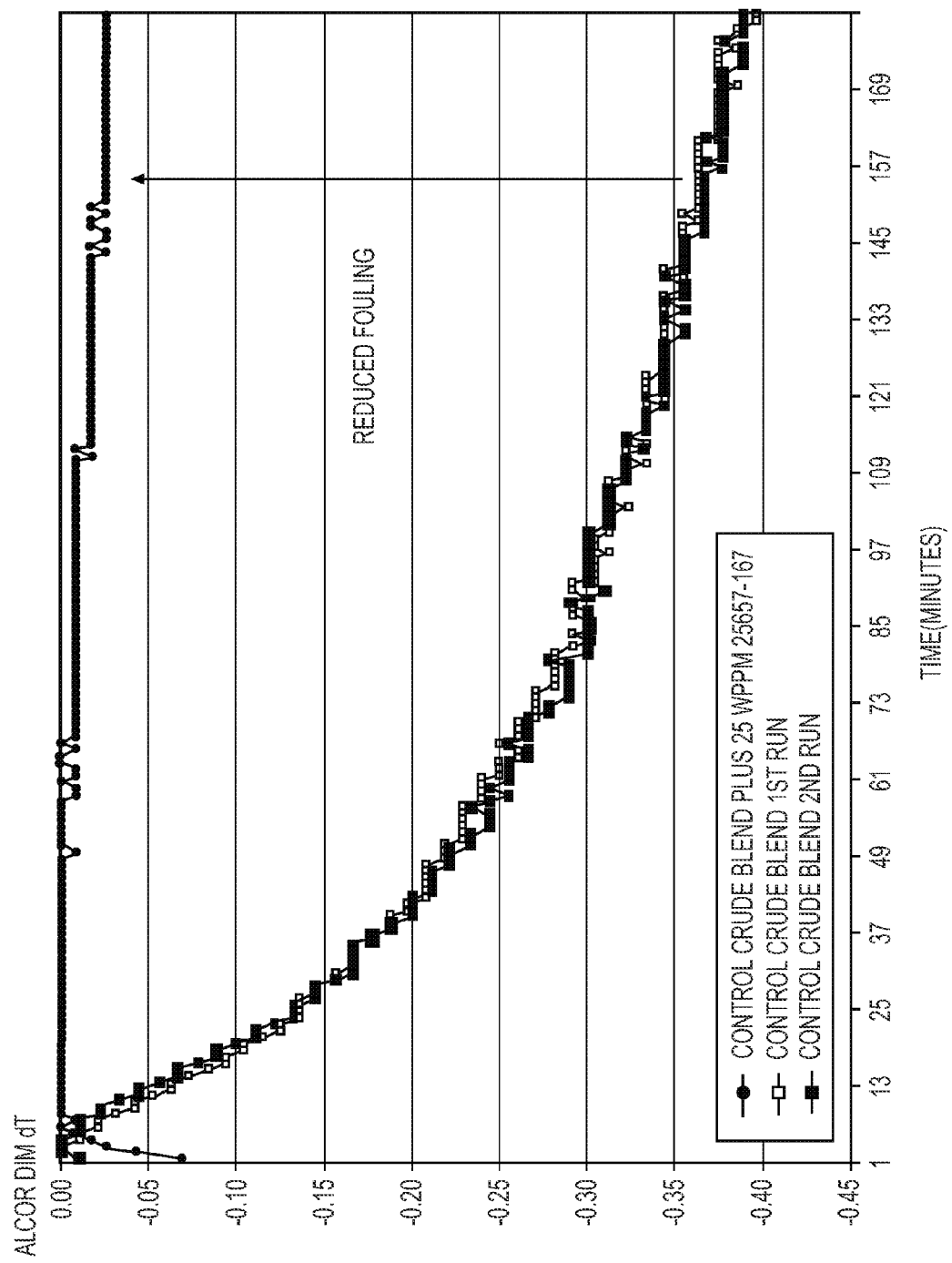
FIG. 5 is a graph demonstrating the effects of fouling of a control crude oil blend sample and a crude oil blend sample treated with 25 wppm of an additive according to the disclosed subject matter, as measured by the Alcor HLPS apparatus depicted in FIG. 2.

FIG. 5 illustrates the impact of fouling of a refinery component over 180 minutes. Two blends were tested in the Alcor unit: a crude oil control containing added rust (iron oxide) particles (200 wppm) without an additive, and the same stream with 25 wppm of the additive prepared in Example 1M. As FIG. 5 demonstrates, the reduction in the outlet temperature over time (due to fouling) is less for the process blend containing the additive as compared to the crude oil control without the additive. This indicates that the additive is effective at reducing fouling of a heat exchanger.

Example 2D

Figure 6:
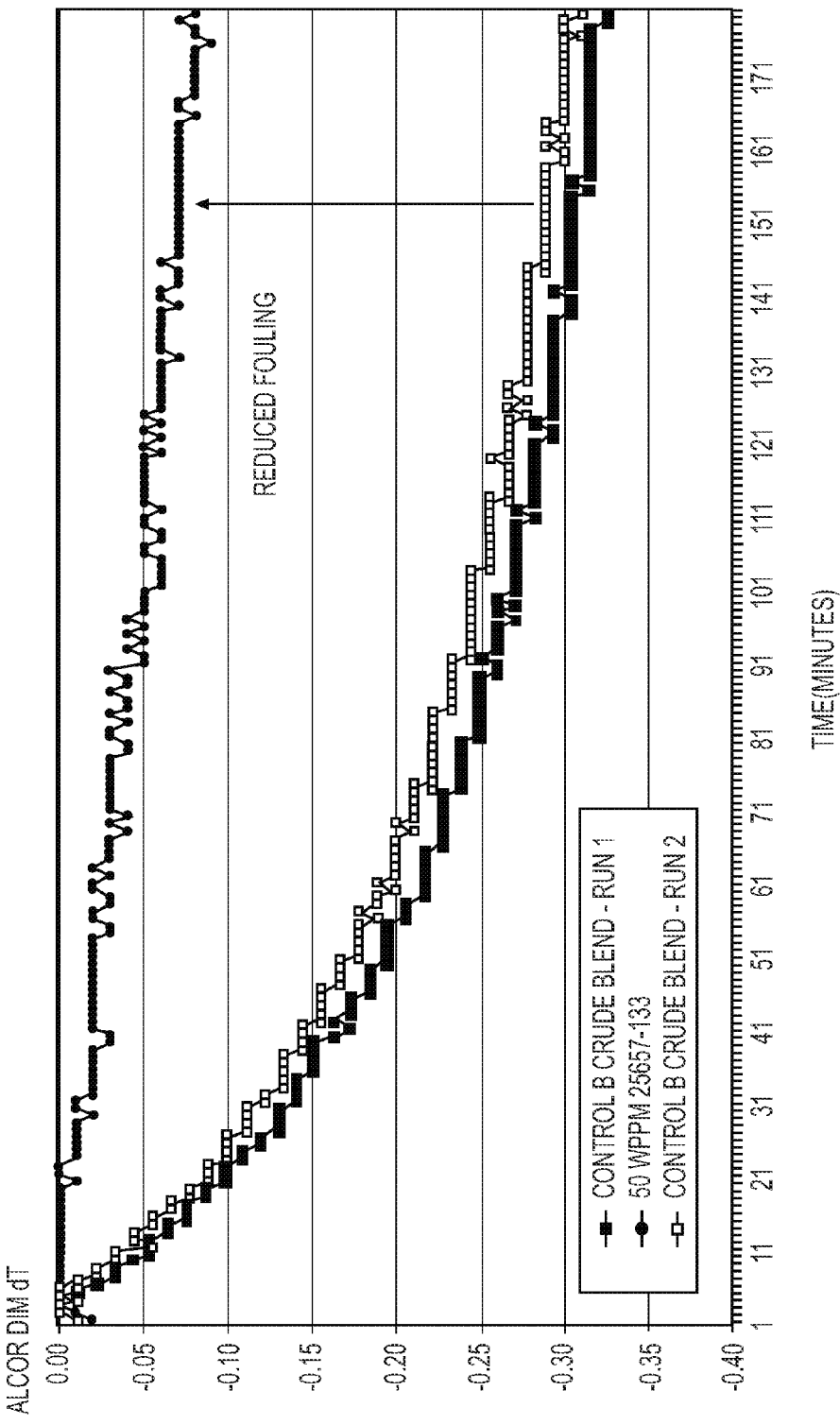
FIG. 6 is a graph demonstrating the effects of fouling of a control crude oil blend sample and a crude oil blend sample treated with 50 wppm of an additive according to the disclosed subject matter, as measured by the Alcor HLPS apparatus depicted in FIG. 2.

FIG. 6 illustrates the impact of fouling of a refinery component over 180 minutes. Two blends were tested in the Alcor unit: a crude oil control containing added rust (iron oxide) particles (200 wppm) without an additive, and the same stream with 50 wppm of the additive prepared in Example 1T. As FIG. 6 demonstrates, the reduction in the outlet temperature over time (due to fouling) is less for the process blend containing the additive as compared to the crude oil control without the additive. This indicates that the additive is effective at reducing fouling of a heat exchanger.

Example 2E

Figure 7:
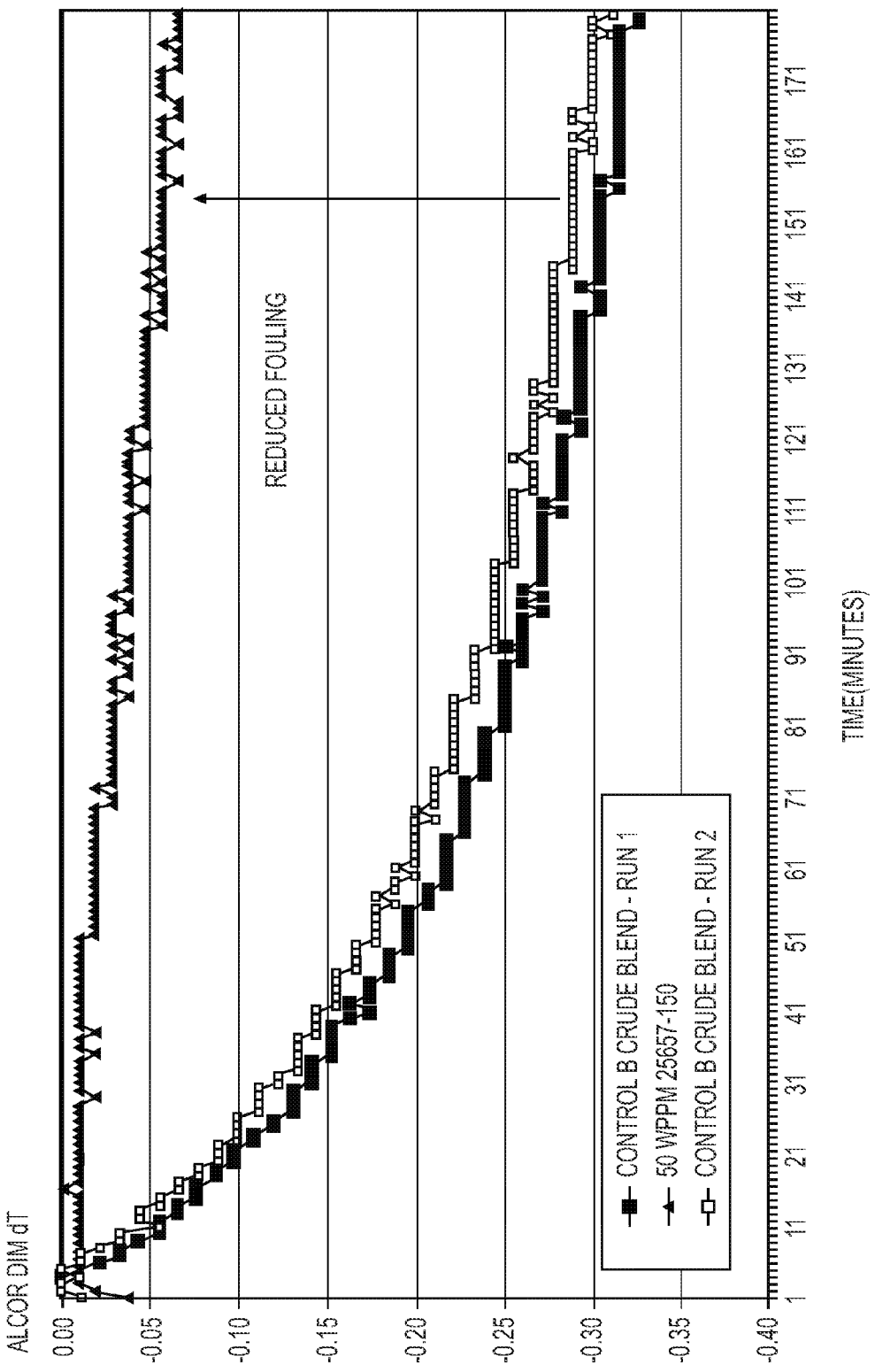
FIG. 7 is a graph demonstrating the effects of fouling of a control crude oil blend sample and a crude oil blend sample treated with 50 wppm of an additive according to the disclosed subject matter, as measured by the Alcor HLPS apparatus depicted in FIG. 2.

FIG. 7 illustrates the impact of fouling of a refinery component over 180 minutes. Two blends were tested in the Alcor unit: a crude oil control containing added rust (iron oxide) particles (200 wppm) without an additive, and the same stream with 50 wppm of the additive prepared in Example 1U. As FIG. 7 demonstrates, the reduction in the outlet temperature over time (due to fouling) is less for the process blend containing the additive as compared to the crude oil control without the additive. This indicates that the additive is effective at reducing fouling of a heat exchanger.

Example 2F

Figure 8:
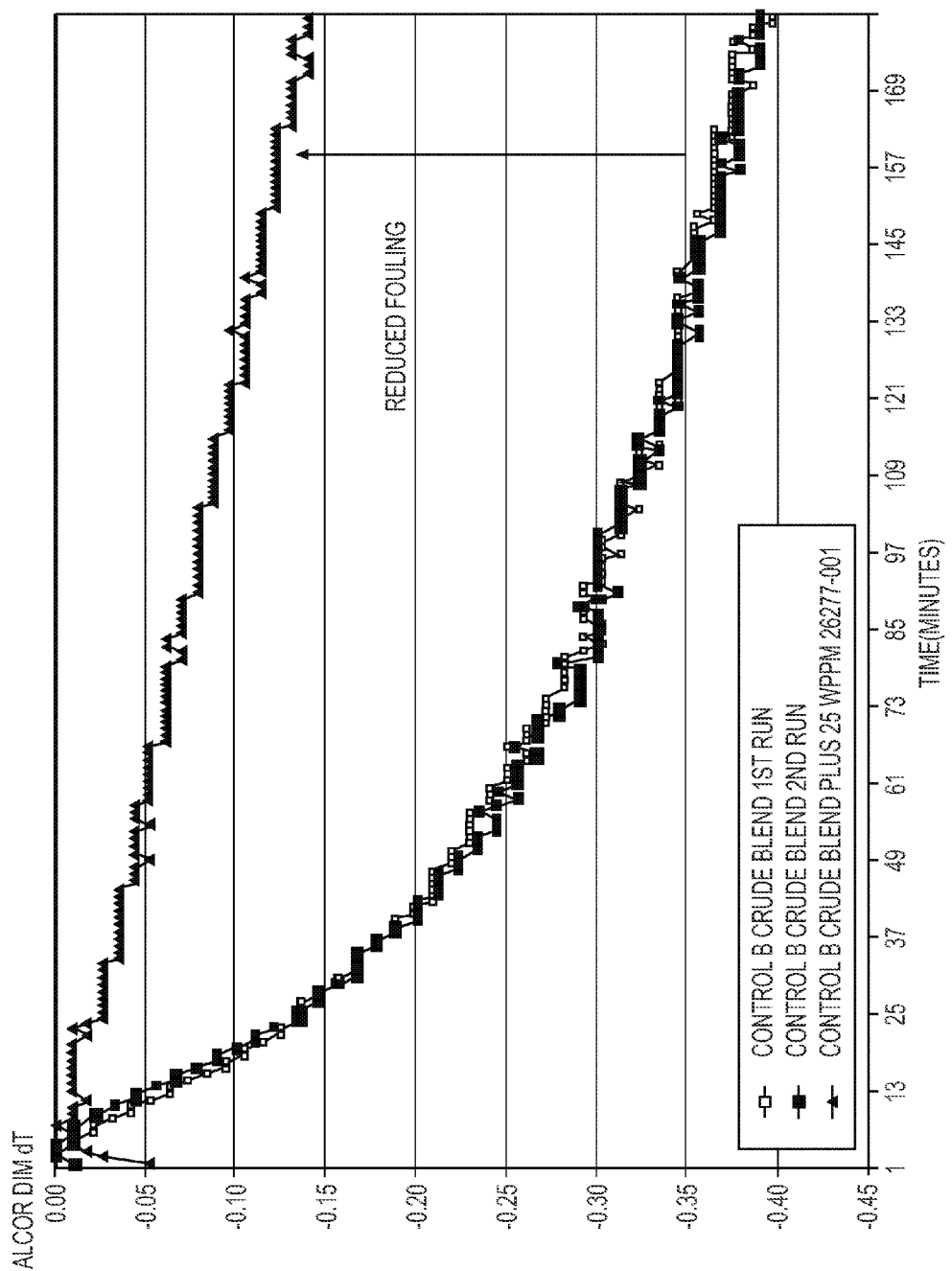
FIG. 8 is a graph demonstrating the effects of fouling of a control crude oil blend sample and a crude oil blend sample treated with 50 wppm of an additive according to the disclosed subject matter, as measured by the Alcor HLPS apparatus depicted in FIG. 2.

FIG. 8 illustrates the impact of fouling of a refinery component over 180 minutes. Two blends were tested in the Alcor unit: a crude oil control containing added rust (iron oxide) particles (200 wppm) without an additive, and the same stream with 25 wppm of the additive prepared in Example 1V. As FIG. 8 demonstrates, the reduction in the outlet temperature over time (due to fouling) is less for the process blend containing the additive as compared to the crude oil control without the additive. This indicates that the additive is effective at reducing fouling of a heat exchanger.

Example 2G

FIG. 9 illustrates the impact of fouling of a refinery component over 180 minutes. Two blends were tested in the Alcor unit: a crude oil control containing added rust (iron oxide) particles (200 wppm) without an additive, and the same stream with 25 ppm and 50 wppm of the additive prepared in Example 1U. As FIG. 9 demonstrates, the reduction in the outlet temperature over time (due to fouling) is less for the process blend containing the additive as compared to the crude oil control without the additive. This indicates that the additive is effective at reducing fouling of a heat exchanger.

* * *

Additional Embodiments

Additionally or alternately, the invention can include one or more of the following embodiments.

Embodiment 1: A compound for treating an emulsion of crude hydrocarbon and/or reducing fouling of a crude hydrocarbon in a hydrocarbon refining process, the compound represented by:

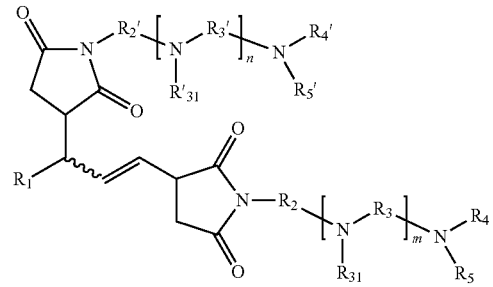

(Formula A)

wherein: m and n are each independently selected from an integer between 0 and 10 inclusive; $R_1$ is a branched or straight-chained $C_{10}$-$C_{800}$ alkyl or alkenyl group; $R_2$ is a $C_1$-$C_4$ branched or straight chained alkylene group; $R_3$ is a $C_1$-$C_4$ branched or straight chained alkylene group; $R_{31}$ is hydrogen or —$R_8$—$R_9$, wherein $R_8$ is $C_1$-$C_4$ branched or straight chained alkylene group, and $R_9$ is

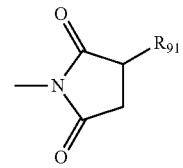

wherein $R_{91}$ is a branched or straight-chained $C_{10}$-$C_{800}$ alkyl or alkenyl group; or $R_8$ and $R_9$ together are a $C_1$-$C_4$ branched or straight chained alkyl group optionally substituted with one or more amine groups; and further wherein the —N($R_{31}$)—$R_3$— repeat unit is optionally interrupted in one or more places by a nitrogen-containing heterocyclic cycloalkyl group; and $R_4$ and $R_5$ are each independently selected from (a) hydrogen; (b) a bond connected to $R_{31}$ in the last distal —N($R_{31}$)—$R_3$— repeat unit; or (c) —$R_6$—$R_7$, wherein $R_6$ is $C_1$-$C_4$ branched or straight chained alkylene group, and $R_7$ is

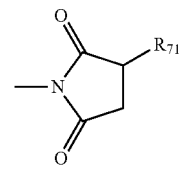

wherein $R_{71}$ is a branched or straight-chained $C_{10}$-$C_{800}$ alkyl or alkenyl group; and wherein the groups $R_2'$, $R_3'$, $R_{31}'$, $R_4'$ and $R_5'$ are each defined the same as $R_2$, $R_3$, $R_{31}$ and $R_4$, and $R_5$, respectively.

Embodiment 2: A compound for treating an emulsion of crude hydrocarbon and/or reducing fouling of a crude hydrocarbon in a hydrocarbon refining process, the compound represented by:

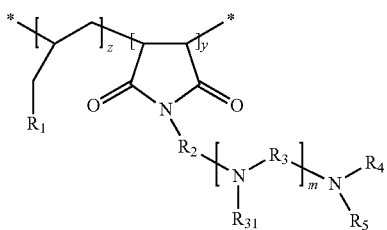

(Formula B)

wherein: m is an integer between 0 and 10 inclusive;
z is 1 or 2, and y is an integer between 1 and 5 inclusive;
$R_1$ is a branched or straight-chained $C_{10}$-$C_{800}$ alkyl or alkenyl group; $R_2$ is a $C_1$-$C_4$ branched or straight chained alkylene group; $R_3$ is a $C_1$-$C_4$ branched or straight chained alkylene group; $R_{31}$ is hydrogen or —$R_8$—$R_9$, wherein $R_8$ is $C_1$-$C_4$ branched or straight chained alkylene group, and $R_9$ is

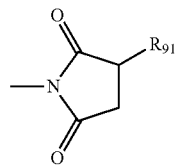

wherein $R_{91}$ is a branched or straight-chained $C_{10}$-$C_{800}$ alkyl or alkenyl group; or $R_8$ and $R_9$ together are a $C_1$-$C_4$ branched or straight chained alkyl group optionally substituted with one or more amine groups; and further wherein the —$N(R_{31})$—$R_3$— repeat unit is optionally interrupted in one or more places by a nitrogen-containing heterocyclic cycloalkyl group; and $R_4$ and $R_5$ are each independently selected from (a) hydrogen; (b) a bond connected to $R_{31}$ in the m-th —$N(R_{31})$—$R_3$— repeat unit; or (c) —$R_6$—$R_7$, wherein $R_6$ is $C_1$-$C_4$ branched or straight chained alkylene group, and $R_7$ is

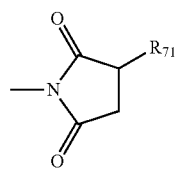

wherein $R_{71}$ is a branched or straight-chained $C_{10}$-$C_{800}$ alkyl or alkenyl group.

Embodiment 3: The compound according to any one of Embodiment 1 or Embodiment 2, wherein at least one of $R_1$, $R_{71}$, and $R_{91}$ comprises polypropylene.

Embodiment 4: The compound according to Embodiment 3, wherein the polypropylene is selected from the group consisting of atactic polypropylene, isotactic polypropylene, syndiotactic polypropylene, amorphous polypropylene, polypropylene including isotactic crystallizable units, polypropylene including syndiotactic crystallizable units, and polypropylene including meso diads constituting from about 30% to about 99.5% of the total diads of the polypropylene.

Embodiment 5: The compound of Embodiment 3, wherein at least one of $R_1$, $R_{71}$, and $R_{91}$ has a number-averaged molecular weight of from about 300 to about 30000 g/mol.

Embodiment 6: The compound of any one of Embodiment 1 or Embodiment 2, wherein at least one of $R_1$, $R_{71}$, and $R_{91}$ comprises polyethylene.

Embodiment 7: The compound of claim any one of Embodiment 1 or Embodiment 2, wherein at least one of $R_1$, $R_{71}$, and $R_{91}$ comprises poly(ethylene-co-propylene).

Embodiment 8: The compound of Embodiment 7, wherein at least one of $R_1$, $R_{71}$, and $R_{91}$ comprises from about 1 mole % to about 90 mole % of ethylene units and from about 99 mole % to about 10 mole % propylene units.

Embodiment 9: The compound of Embodiment 8, wherein at least one of $R_1$, $R_{71}$, and $R_{91}$ comprises from about 10 mole % to about 50 mole % of ethylene units.

Embodiment 10: The compound of any one of Embodiment 1 or Embodiment 2, wherein at least one of $R_1$, $R_{71}$, and $R_{91}$ comprises poly(higher alpha-olefin), the higher alpha-olefin including two or more carbon atoms on each side chain.

Embodiment 11: The compound of any one of Embodiment 1 or Embodiment 2, wherein at least one of $R_1$, $R_{71}$, and $R_{91}$ comprises polypropylene-co-higher alpha-olefin), the higher alpha-olefin including two or more carbon atoms on each side chain.

Embodiment 12: The compound of any one of Embodiment 1 or Embodiment 2, wherein the nitrogen content in the compound is about 1 wt % to about 10 wt % of the total weight of the compound.

Embodiment 13: The compound of any one of Embodiment 1 or Embodiment 2, wherein $R_3$ is —$CH_2$—$CH_2$—, and $R_{31}$ is hydrogen.

Embodiment 14: The compound of Embodiment 13, wherein the —$N(R_{31})$—$R_3$— repeat unit is interrupted in one or more places by a 1,4-diethylenediamine.

Embodiment 15: A method for reducing fouling in a hydrocarbon refining process comprising providing a crude hydrocarbon for a refining process; and adding an additive to the crude hydrocarbon, wherein the additive is selected from one of the compounds set forth in any one of Embodiments 1-14.

Embodiment 16: A method for preparing a compound for treating an emulsion of crude hydrocarbon and/or reducing fouling of a crude hydrocarbon in a hydrocarbon refining process, comprising:

(a) reacting a polymer base unit $R_{11}$, which is a branched or straight-chained $C_{10}$-$C_{800}$ alkyl or alkenyl group having a vinyl terminal group, with maleic anhydride to obtain a polymer represented by Formula I below:

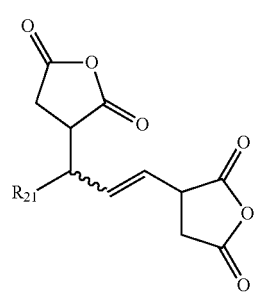

(I)

wherein $R_{21}$ is a branched or straight-chained $C_{10}$-$C_{800}$ alkyl or alkenyl group;

(b) reacting the polymer obtained in (a) with a polyamine represented by

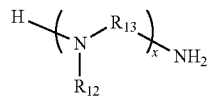

wherein $R_{12}$ is hydrogen or a $C_1$-$C_4$ branched or straight chained alkyl optionally substituted with one or more amine groups, $R_{13}$ is a $C_1$-$C_4$ branched or straight chained alkylene group, and x is an integer between 1 and 10, and further wherein the —N($R_{12}$)—$R_{13}$— unit is optionally interrupted in one or more places by a nitrogen-containing heterocyclic cycloalkyl group, and wherein when the x-th —N($R_{12}$)—$R_{13}$— unit along with the terminal nitrogen atom forms a heterocyclic cycloalkyl group, the terminal —NH$_2$ is replaced by a —NH— group for valency.

Embodiment 17: A method for preparing a compound for treating an emulsion of crude hydrocarbon and/or reducing fouling of a crude hydrocarbon in a hydrocarbon refining process, the method comprising:

(a) reacting a polymer base unit $R_{11}$, which is a branched or straight-chained $C_{10}$-$C_{800}$ alkyl or alkenyl group having a vinyl terminal group, with maleic anhydride to obtain a polymer represented by Formula II below:

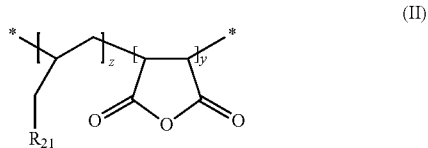

(II)

wherein $R_{21}$ is a branched or straight-chained $C_{10}$-$C_{800}$ alkyl or alkenyl group, z is 1 or 2, and y is an integer between 1 and 5 inclusive;

(b) reacting the polymer obtained in (a) with a polyamine represented by

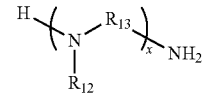

wherein $R_{12}$ is hydrogen or a $C_1$-$C_4$ branched or straight chained alkyl optionally substituted with one or more amine groups, $R_{13}$ is a $C_1$-$C_4$ branched or straight chained alkylene group, and x is an integer between 1 and 10, and further wherein the —N($R_{12}$)—$R_{13}$-unit is optionally interrupted in one or more places by a nitrogen-containing heterocyclic cycloalkyl group, and wherein when the x-th —N($R_{12}$)—$R_{13}$— unit along with the terminal nitrogen atom forms a heterocyclic cycloalkyl group, the terminal —NH$_2$ is replaced by a —NH— group for valency.

Embodiment 18: The method according to any one of Embodiment 16 and Embodiment 17, wherein the molar ratio of $R_{11}$:polyamine is between about 5:1 and about 1:1.

Embodiment 19: The method according to any one of Embodiment 16 and Embodiment 17, wherein at least 50% of the terminal vinyl groups of $R_{11}$ are an allylic vinyl group.

Embodiment 20: The method according to any one of Embodiment 16 and Embodiment 17, wherein the polyamine comprises linear, branched or cyclic isomers of an oligomer of ethyleneamine, or mixtures thereof, wherein each two neighboring nitrogens in the oligomer of ethyleneamine are bridged by one or two ethyleneamine groups.

Embodiment 21: The method according to Embodiment 20, wherein the polyamine is selected from ethylenediamine, diethylenetriamine, triethylenetetramine, tetraethylenepentamine, pentaethylenehexamine, hexaethyleneheptamine, and mixtures thereof Embodiment 22: The method according to any one of Embodiment 16 and Embodiment 17, wherein the polyamine comprises a heavy polyamine Embodiment 23: The method according to any one of Embodiment 16 and Embodiment 17, wherein (a) comprises reacting the polymer base unit $R_{11}$ with maleic anhydride at a ratio $R_{11}$:maleic anhydride of between about 1:1 to about 1:5.

Embodiment 24: The method according to any one of Embodiment 16 and Embodiment 17, wherein (a) comprises reacting the polymer base unit $R_{11}$ with maleic anhydride without an additional initiator providing a radical species.

Embodiment 25: A compound for reducing fouling of a crude hydrocarbon in a hydrocarbon refining process, the compound prepared by the method according to any one of Embodiments 16 and 18-24.

Embodiment 26: A compound for treating an emulsion of crude hydrocarbon and/or reducing fouling of a crude hydrocarbon in a hydrocarbon refining process, the compound prepared by the method according to any one of Embodiments 17-24.

* * *

The disclosed subject matter is not to be limited in scope by the specific embodiments described herein. Indeed, various modifications of the invention in addition to those described herein will become apparent to those skilled in the art from the foregoing description and the accompanying figures. Such modifications are intended to fall within the scope of the appended claims It is further to be understood that all values are approximate, and are provided for description.

Patents, patent applications, publications, product descriptions, and protocols are cited throughout this application, the disclosures of each of which is incorporated herein by reference in its entirety for all purposes.

The invention claimed is:

1. A method for reducing fouling in a hydrocarbon refining process comprising providing a crude hydrocarbon for a refining process; and
adding an additive to the crude hydrocarbon, the additive selected from the group consisting of:

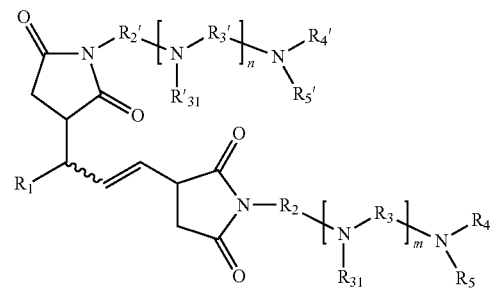

(Formula A)

wherein:

m is an integer between 0 and 10 inclusive;

$R_1$ is a branched or straight-chained $C_{10}$-$C_{800}$ alkyl or alkenyl group;

$R_2$ is a $C_1$-$C_4$ branched or straight chained alkylene group;

$R_3$ is a $C_1$-$C_4$ branched or straight chained alkylene group:, $R_{31}$ is hydrogen or —$R_8$—$R_9$, wherein $R_8$ is $C_1$-$C_4$ branched or straight chained alkylene group, and $R_9$ is

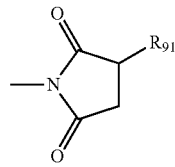

wherein $R_{91}$ is a branched or straight-chained $C_{10}$-$C_{800}$ alkyl or alkenyl group; or $R_8$ and $R_9$ together are a $C_1$-$C_4$ branched or straight chained alkyl group optionally substituted with one or more amine groups; and further wherein the —$N(R_{31})$—$R_3$— repeat unit is optionally interrupted in one or more places y a nitrogen-containing heterocyclic cycloalkyl group:, and $R_4$ and $R_5$ are each independently selected from (a) hydrogen; (b) a bond connected to $R_{31}$ in the m-th —$N(R_{31})$—$R_3$— repeat unit; or (c) —$R_6$—$R_7$, wherein $R_6$ is $C_1$-$C_4$ branched or straight chained alkylene group, and $R_7$ is

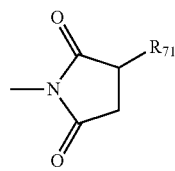

wherein $R_{71}$ is a branched or straight-chained $C_{10}$-$C_{800}$ alkyl or alkenyl group, wherein, n is an integer between 0 and 10 inclusive, and the groups $R_2'$, $R_3'$, $R_{31}'$, $R_4'$ and $R_5'$ are each defined the same as $R_2$, $R_3$, $R_{31}$ and $R_4$, and $R_5$, respectively, and wherein at least one of $R_1$, $R_{71}$, and $R_{91}$ comprises polyethylene.

2. A method for the reducing fouling in a hydrocarbon refining process comprising
providing a crude hydrocarbon for a refining process; and
adding an additive to the crude hydrocarbon, the additive selected from the group consisting of:

(Formula A)

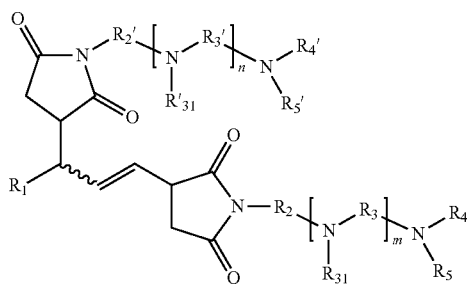

wherein:

m is an integer between 0 and 10 inclusive;

$R_1$ is a branched or straight-chained $C_{10}$-$C_{800}$ alkyl or alkenyl group;

$R_2$ is a $C_1$-$C_4$ branched or straight chained alkylene group;

$R_3$ is a $C_1$-$C_4$ branched or straight chained alkylene group;

$R_{31}$ is hydrogen or —$R_8$—$R_9$, wherein $R_8$ is $C_1$-$C_4$ branched or straight chained alkylene group, and $R_9$ is

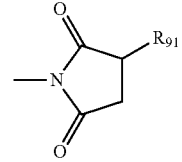

wherein $R_{91}$ is a branched or straight-chained $C_{10}$-$C_{800}$ alkyl or alkenyl group; or $R_8$ and $R_9$ together are a $C_1$-$C_4$ branched or straight chained alkyl group optionally substituted with one or more amine groups; and further wherein the —$N(R_{31})$—$R_3$— repeat unit is optionally interrupted in one or more places by a nitrogen-containing heterocyclic cycloalkyl group; and $R_4$ and $R_5$ are each independently selected from (a) hydrogen; (b) a bond connected to $R_{31}$ in the m-th —$N(R_{31})$—$R_3$— repeat unit; or (c) —$R_6$—$R_7$, wherein $R_6$ is $C_1$-$C_4$ branched or straight chained alkylene group, and $R_7$ is

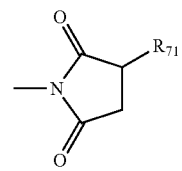

wherein $R_{71}$ is a branched or straight-chained $C_{10}$-$C_{800}$ alkyl or alkenyl group, wherein, n is an integer between 0 and 10 inclusive, and the groups $R_2'$, $R_3'$, $R_{31}'$, $R_4'$ and $R_5'$ are each defined the same as $R_2$, $R_3$, $R_{31}$ and $R_4$, and $R_5$, respectively, and wherein at least one of $R_1$, $R_{71}$, and $R_{91}$ comprises poly(ethytene-co-propylene).

3. The method of claim 2, wherein at least one of $R_1$, $R_{71}$, and $R_{91}$ comprises from about 1 mole % to about 90 mole % of ethylene units and from about 99 mole % to about 10 mole % propylene units.

4. The method of claim 3, wherein at least one of $R_1$, $R_{71}$, and $R_{91}$ comprises from about 10 mole % to about 50 mole % of ethylene units.

5. A method for reducing fouling in a hydrocarbon refining process comprising
providing a crude hydrocarbon for a refining process; and
adding an additive to the crude hydrocarbon, the additive selected from the group consisting of:

(Formula A)

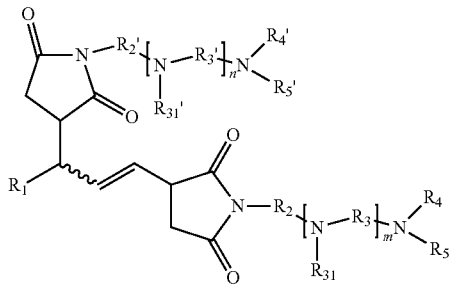

wherein:

m is an integer between 0 and 10 inclusive;

$R_1$ is a branched or straight-chained $C_{10}$-$C_{800}$ alkyl or alkenyl group;

$R_2$ is a $C_1$-$C_4$ branched or straight chained alkylene group;

$R_3$ is a $C_1$-$C_4$ branched or straight chained alkylene group;

$R_{31}$ is hydrogen or —$R_8$—$R_9$, wherein $R_8$ is $C_1$-$C_4$ branched or straight chained alkylene group, and $R_9$ is

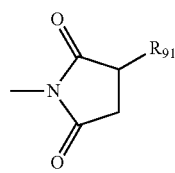

wherein $R_{91}$ is a branched or straight-chained $C_{10}$-$C_{800}$ alkyl or alkenyl group; or $R_8$ and $R_9$ together are a $C_1$-$C_4$ branched or straight chained alkyl group optionally substituted with one or more amine groups; and further wherein the —N($R_{31}$)—$R_3$— repeat unit is optionally interrupted in one or more places by a nitrogen-containing heterocyclic cycloalkyl group; and $R_4$ and $R_5$ are each independently selected from (a) hydrogen; (b) a bond connected to $R_{31}$ in the m-th —N($R_{31}$)—$R_3$— repeat unit; or (c) —$R_6$—$R_7$, wherein $R_6$ is $C_1$-$C_4$ branched or straight chained alkylene group, and $R_7$ is

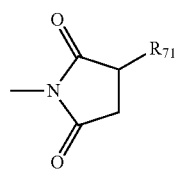

wherein $R_{71}$ is a branched or straight-ehained $C_{10}$-$C_{800}$ alkyl or alkenyl group, wherein, n is an integer between 0 and 10 inclusive, and the groups $R_2'$, $R_3'$, $R_{31}'$, $R_4'$ and $R_5'$ are each defined the same as $R_2$, $R_3$, $R_{31}$ and $R_4$, and $R_5$, respectively, and wherein at least one of $R_1$, $R_{71}$, and $R_{91}$ comprises poly(propylene-co-higher alpha-olefin), the higher alpha-olefin including two or more carbon atoms on each side chain.

6. The method of claim 1 or 2 or 5, wherein at least one of $R_1$, $R_{71}$, and $R_{91}$ has a number-averaged molecular weight of from about 300 to about 30000 g/mol.

7. The method of claim 1, or 2, or 5, wherein the nitrogen content in the compound is about 1 wt % to about 10 wt % based on the total weight of the compound.

8. A method for reducing fouling in a hydrocarbon refining process comprising
providing a crude hydrocarbon for a refining process; and
adding an additive to the crude hydrocarbon, the additive selected from the group consisting of:

(Formula A)

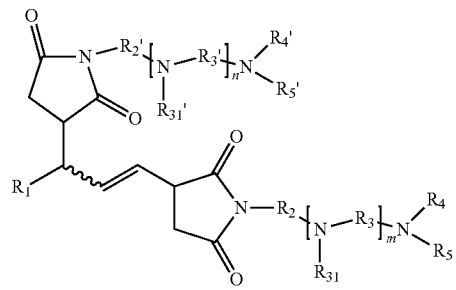

wherein:

m is an integer between 0 and 10 inclusive;

$R_1$ is a branched or straight-chained $C_{10}$-$C_{800}$ alkyl or alkenyl group;

$R_2$ is a $C_1$-$C_4$ branched or straight chained alkylene group;

$R_3$ is a $C_1$-$C_4$ branched or straight chained alkylene group;

$R_{31}$ is hydrogen or —$R_8$—$R_9$, wherein $R_8$ is $C_1$-$C_4$ branched or straight chained alkylene group, and $R_9$ is

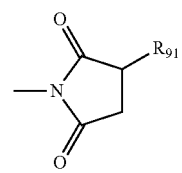

wherein $R_{91}$ is a branched or straight-chained $C_{10}$-$C_{800}$ alkyl or alkenyl group or $R_8$ and $R_9$ together are a $C_1$-$C_4$ branched or straight chained alkyl group optionally substituted with one or more amine groups; and further wherein the —N($R_{31}$)—$R_3$— repeat unit is optionally interrupted in one or more places by a nitrogen-containing heterocyclic cycloalkyl group; and $R_4$ and $R_5$ are each independently selected from (a) hydrogen; (b) a bond connected to $R_{31}$ in the m-th —N($R_{31}$)—$R_3$— repeat unit; or (c) —$R_6$—$R_7$, wherein $R_6$ $C_1$-$C_4$ branched or straight chained alkylene group, and $R_7$ is

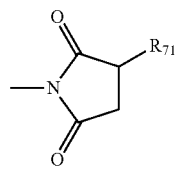

wherein $R_{71}$ is a branched or straight-chained $C_{10}$-$C_{800}$ alkyl or alkenyl group, wherein, n is an integer between 0 and 10 inclusive, and the groups $R_2'$, $R_3'$, $R_{31}'$, $R_4'$ and $R_5'$ are each defined the same as $R_2$, $R_3$, $R_{31}$ and $R_4$, and $R_5$, respectively, wherein $R_3$ is —$CH_2$—$CH_2$—, and $R_{31}$ is hydrogen; and wherein the —$N(R_{31})$—$R_3$— repeat unit is interrupted in one or more places by a 1,4-diethylenediamine.

* * * * *